(12) United States Patent
Camire et al.

(10) Patent No.: US 8,236,764 B2
(45) Date of Patent: Aug. 7, 2012

(54) METHODS FOR TREATING A HEMOSTASIS RELATED DISORDER USING ACTIVATED FORMS OF FACTOR V

(75) Inventors: Rodney M. Camire, Sicklerville, NJ (US); Valder R. Arruda, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 94 days.

(21) Appl. No.: 12/162,935

(22) PCT Filed: Feb. 23, 2007

(86) PCT No.: PCT/US2007/062720
§ 371 (c)(1),
(2), (4) Date: Oct. 27, 2008

(87) PCT Pub. No.: WO2007/101106
PCT Pub. Date: Sep. 7, 2007

(65) Prior Publication Data
US 2009/0318344 A1    Dec. 24, 2009

Related U.S. Application Data

(60) Provisional application No. 60/776,124, filed on Feb. 23, 2006.

(51) Int. Cl.
*A61K 38/36* (2006.01)
*A61K 38/37* (2006.01)
*C07K 14/745* (2006.01)

(52) U.S. Cl. .......................... 514/12; 530/381

(58) Field of Classification Search ................. None
See application file for complete search history.

(56) References Cited

FOREIGN PATENT DOCUMENTS
WO      03/100053      12/2003

OTHER PUBLICATIONS

Camire, R., et al. "Characterization of B-domain elements which maintain factor V in a procofactor form." Database Biosis [Online]. Nov. 2004.
Kolfschoten, M., et al. "Factor Va is inactivated by activated protein C in the absence of cleavage sites at Arg-306, Arg-506 and Arg-679." J Biol Chem. Feb. 20, 2004;279(8):6567-6575.
Arbini, A. A., et al. "Low Prevalence of the Factor V Leiden Mutation Among 'Severe' Hemophiliacs with a 'Milder' Bleeding Diathesis." Thrombosis and Haemostasis, 74(5): 1255-8 (1995).
Arruda, V. R., et al. "Association of severe haemophilia a and factor V Leiden: report of three cases." Haemophilia, 2(1): 51-53 (1996).
Bos, M. H. A. et al. "Does activated protein C-resistant factor V contribute to thrombin generation in hemophilic plasma?" Journal of Thrombosis and Haemostasis, 3(2): 522-530 (Mar. 2005).
Ettingshausen, C. E., et al. "Symptomatic Onset of Severe Hemophilia A in Childhood is Dependent on the Presence of Prothrombotic Risk Factors." Thrombosis and Haemostasis, 85: 218-20 (2001).
Lee, H., et al. "Effect of the Factor V Leiden Mutation on the Clinical Expression of Severe Hemophilia A." Thrombosis and Haemostasis, 83: 387-91 (2000).
Nichols, WC, et al. "Moderation of hemophilia A phenotype by the factor V R506Q mutation." Blood, 88: 1183-1187 (1996).

(Continued)

*Primary Examiner* — Ruixiang Li
(74) *Attorney, Agent, or Firm* — Dann, Dorfman, Herrell & Skillman; Kathleen D. Rigaut

(57) ABSTRACT

Methods for the treatment of coagulation disorders using Factor V/Va variants are provided.

7 Claims, 5 Drawing Sheets

Factor V
$M_r = 330,000$

Factor V-810
$M_r = 216,000$

Factor Va

Heavy Chain: $M_r = 105,000$     Light Chain: $M_r = 74,000$

OTHER PUBLICATIONS

Schlachterman, A., et al. "Factor V Leiden improves in vivo hemostasis in murine hemophilia models." Journal of Thrombosis and Haemostasis, 3(12): 2730-2737 (Dec. 2005).

Toso, R., of al. "Removal of B-domain Sequences from Factor V Rather than Specific Proteolysis Underlies the Mechanism by Which Cofactor Function is Realized." Journal of Biological Chemistry, 279(20): 21643-21650 (May 14, 2004).

Van't Veer, C., et al. "An in Vitro Analysis of the Combination of Hemophilia A and Factor V Leiden." Blood, 90: 3067-3072 (1997).

Schlachterman, A., et al. "Factor V Leiden improves in vivo hemostasis in murine hemophilia models." Journal of Thrombosis and Haemostasis, 3: 2130-2737 (Dec. 2005).

Toso, R., et al. "Removal of B-domain Sequences from Factor V Rather than Specific Proteolysis Underlies the Mechanism by Which Cofactor Function Is Realized." Journal of Biological Chemistry, 279(20): 21643-21650 (May 14, 2004).

METHODS FOR TREATING A HEMOSTASIS RELATED DISORDER USING ACTIVATED FORMS OF FACTOR V

The present application is §371 application of PCT/US2007/062720 filed 23 Feb. 2007 which claims priority to U.S. Provisional Application No. 60/776,124 filed 23 Feb. 2006, the entire disclosure of each being incorporated by reference herein.

Pursuant to 35 U.S.C. §202(c), it is acknowledged that the U.S. Government has certain rights in the invention described herein, which was made in part with funds from the National Institutes of Health, Grant Number K01 DK60580-01 and P01-HL74124-01 (Project 2).

FIELD OF THE INVENTION

The present invention relates the fields of medicine and hematology. More specifically, the invention describes therapeutic strategies using activated forms of FV and derivatives thereof for modulating the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

Hemophilia is an X-linked hemorrhagic disorder resulting from mutations in either the FVIII (hemophilia A) or FIX (hemophilia B) genes, with an incidence of approximately 1:5,000 male individuals worldwide. Affected individuals commonly present spontaneous hemorrhages and prolonged bleeding after trauma or surgery. Severely affected subjects present FVIII or FIX levels lower than 1% of normal and comprise the majority of clinically symptomatic cases. The remaining patients have mild to moderate disease with factor levels of 1-30%[1].

The clinical presentation of hemophilia is essentially indistinguishable for FVIII or FIX deficiency. However, there is clear evidence that the clinical phenotype of hemophilia varies among patients with similar residual factor levels or even with the same underlying mutation [2-4]. Therefore, it is possible that other genetic or acquired factors influence the hemophilia phenotype. The current understanding of the genetic basis of venous thrombosis provides an opportunity to determine whether these risk factors could improve the hemophilia phenotype.

Thrombin generation is in part controlled by activated protein C (APC), which is formed by limited proteolysis of the zymogen protein C by the thrombin-thrombomodulin complex. The anticoagulant effect of APC results from the inactivation of both factors Va and VIIIa on membrane surfaces [5]. The most common inherited thrombophilia results from a mutation in the FV gene (Arg 506 to Gln) known as FV Leiden (FVL). Because Arg 506 is the initial cleavage site for APC, FVL is inactivated at approximately one tenth the rate of normal FVa [6], which result in high thrombin levels that create a procoagulant state.

FVL is the most commonly investigated modifier of the hemophilia phenotype because it is present in 2-5% of the Caucasian population [7, 8]. Initial reports suggested the amelioration of the severe hemophilia A phenotype among subjects with FVL [9, 10]. Further studies, however, failed to demonstrate the clinical impact of such association. In screening over 700 hemophilia subjects, 35 cases of FVL have been identified. In only half of these cases (14 hemophilia A and 1 hemophilia B) the association was considered beneficial in terms of frequency of bleeds and/or factor consumption over time [9-14]. The reasons for these discrepancies are not clear but could relate to the small number of subjects, differences in age groups, the presence of underlying infectious diseases, and the retrospective nature of the study. The results of a pediatric study have been informative in this matter since many of the complications common among adults are not confounding factors in children. This case-control study demonstrated that among hemophilia A children with FVL or with other thrombophilia risk factors, the onset of the first bleeding episode was delayed [14].

There is also in vitro evidence that the FVL mutation can modify thrombin generation in FVIII [15] or FIX deficient plasma [16]. Moreover, the assessment of the fibrinolytic system in hemophilia revealed that thrombin-induced clots in FVIII or FIX deficient plasma were lysed prematurely [17]. Therefore, the enhanced generation of thrombin by FVL may also increase the resistance of the fibrin clot to premature lysis [18, 19].

SUMMARY OF THE INVENTION

To gain insight into the discrepancies between clinical and laboratory assessments of the impact of FVL on hemophilia, we took advantage of the availability of genetically engineered mice for severe hemophilia and FVL. These murine models provide the opportunity to address the role of this thrombotic risk factor in modifying the hemophiliac phenotype in vivo with minimal influence from environmental factors. Using these unique model systems in conjunction with biochemical assays and real-time imaging of clot formation in living animals, we have found that activated forms of FV can beneficially modify the hemophilia phenotype.

A pharmaceutical composition comprising the activated forms of FV as well as cleavage resistant forms of activated FV of the invention in a biologically compatible carrier which may be directly infused into a patient is also provided. Another preferred aspect of the invention includes methods for the treatment of a hemostasis related disorder in a patient in need thereof comprising administration of a therapeutically effective amount of the activated forms of FV containing pharmaceutical compositions described herein. Such methods should have efficacy in the treatment of disorders where a pro-coagulant is needed and include, without limitation, hemophilia A and B, hemophilia A and B associated with inhibitory antibodies, coagulation factor deficiency, vitamin K epoxide reductase C1 deficiency, gamma-carboxylase deficiency, bleeding associated with trauma, injury, thrombosis, thrombocytopenia, stroke, coagulopathy, disseminated intravascular coagulation (DIC); over-anticoagulation treatment disorders, Bernard Soulier syndrome, Glanzman thromblastemia, and storage pool deficiency.

Another aspect of the invention, includes host cells expressing the variant activated forms of FV of the invention in order to produce large quantities thereof. Methods for isolating and purifying the activated forms of FV are also disclosed.

DETAILED DESCRIPTION OF THE INVENTION

Figure 1:
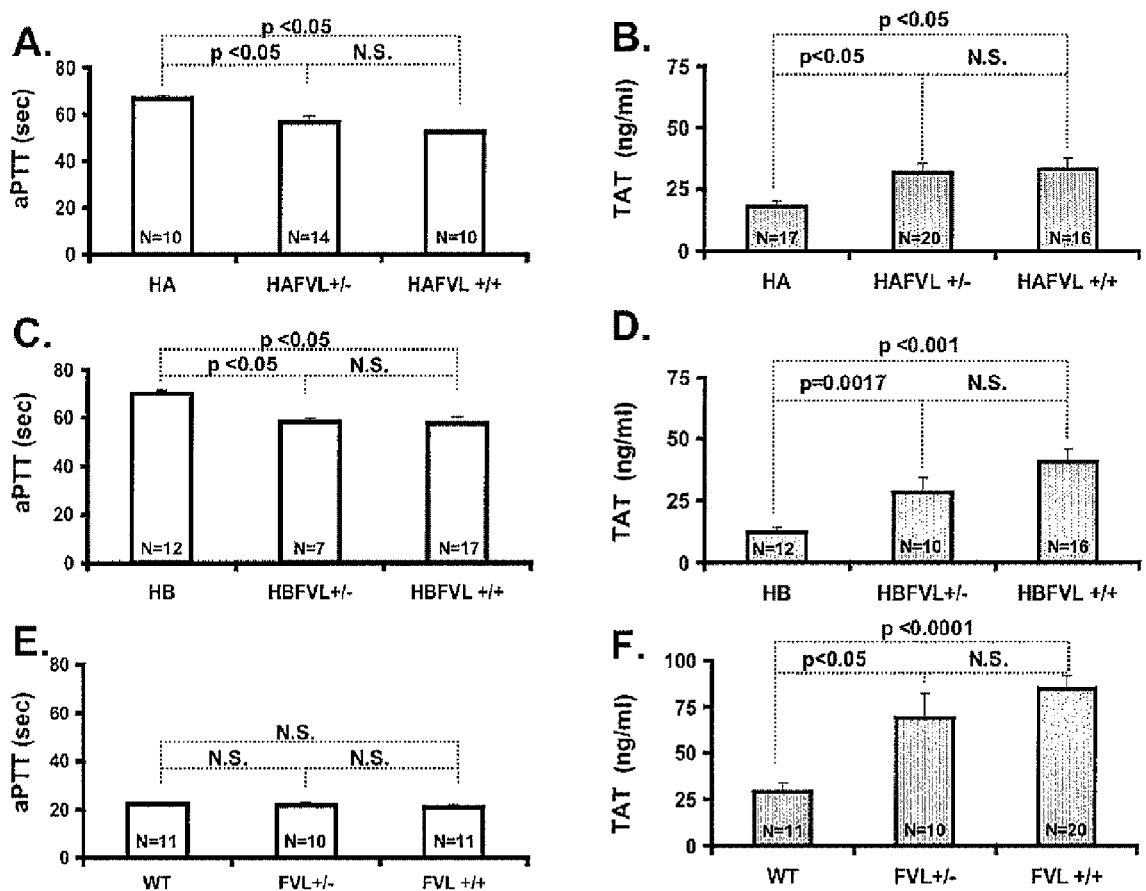
FIG. 1. Clotting assays in murine models of hemophilia or Factor V Leiden (FVL) and in normal controls. Panels A, C, and E: Modified one stage activated partial thromboplastin assay (aPTT) in mouse plasma. Panels B, D and F: Thrombin-antithrombin complex (TAT) levels in mice plasma. The numbers of animals per group are indicated. Adult hemophilia A (HA) or hemophilia B (HB) mice without FVL were compared with animals heterozygous (+/−) or homozygous (+/+) for FVL. P values were calculated by ANOVA. NS: not significant.

The role of factor V Leiden (FVL) as a modifier of the severe hemophilia phenotype is still unclear. We used mice with hemophilia A or B crossed with FVL to elucidate in vivo parameters of hemostasis. Real-time thrombus formation in the microcirculation was monitored by deposition of labeled platelets upon laser-induced endothelial injury using widefield microscopy in living animals. No thrombi formed in hemophilic A or B mice following vascular injuries. However, hemophilic mice, either heterozygous or homozygous for FVL, formed clots at all injured sites. Injection of purified activated FV into hemophilic A or B mice could mimic the in vivo effect of FVL. In contrast to these responses to a laser injury in a microvascular bed, FVL did not provide sustained hemostasis following damage of large vessels in a ferric chloride carotid artery injury model, despite of the improvement of clotting times and high circulating thrombin levels. Together these data provide evidence that FVL has the ability to improve the hemophilia A or B phenotype, but this effect is principally evident at the microcirculation level following a particular vascular injury. Our observations may partly explain the heterogeneous clinical evidence of the beneficial role of FVL in hemophilia.

Thus, in accordance with one aspect of the invention, methods for the treatment of hemophilia are provided. An exemplary method entails administration of an effective amount of an activated form of FV or a derivative thereof to patient to enhance clot formation, thereby ameliorating the symptoms of hemophilia. This treatment initiates coagulation in individuals who lack intrinsic pathway proteins, have inhibitors to these proteins, or who have some other hemostatic abnormality which would benefit by administration of an activated form of FV. Administration of active FV or engineered derivatives of an activated form of FV which have the activated form of FV-like properties to by-pass deficiencies in the intrinsic or extrinsic pathway is disclosed.

Protein replacement therapy using recombinant or plasma-derived forms of factor VIII (or B-domain deleted FVIII), factor IX, or factor VIIa (NovoSeven) is currently the mainstay of hemophilia care. While this treatment regime has limitations, it is very effective and has helped thousands of patients. Over the past 20 years significant progress has been made by several groups in understanding the biochemistry of FV. Factor V circulates in plasma as a single chain procofactor at a concentration of 7 μg/mL (20 nM) and has a half-life of ~12 hours. It is a large ($M_r$=330,000, 2196 amino acids) heavily glycosylated, single chain, multi-domain (A1-A2-B-A3-C1-C2) protein which is synthesized in the liver and is homologous to factor VII. Factor V is secreted as an inactive procofactor and cannot function in the prothrombinase complex (FXa, FVa, anionic membranes, and calcium). This is consistent with the observation that FV binds very weakly, if at all, to FXa and prothrombin, and indicates that proteolytic conversion of FV to FVa leads to appropriate structural changes which impart cofactor function.

Thrombin is established as the most robust activator of FV. Proteolysis occurs at $Arg^{709}$, $Arg^{1018}$, and $Arg^{1545}$ generating $FVa_{IIa}$, a heterodimer composed of an N-terminal 105 kDa heavy chain associated via $Ca^{2+}$ ions to the C-terminal 74/71 kDa light chain. See FIG. 5. The large, heavily glycosylated B domain, spanning amino acids 710-1545, is not necessary for cofactor activity and is released during activation.

Figure 5:
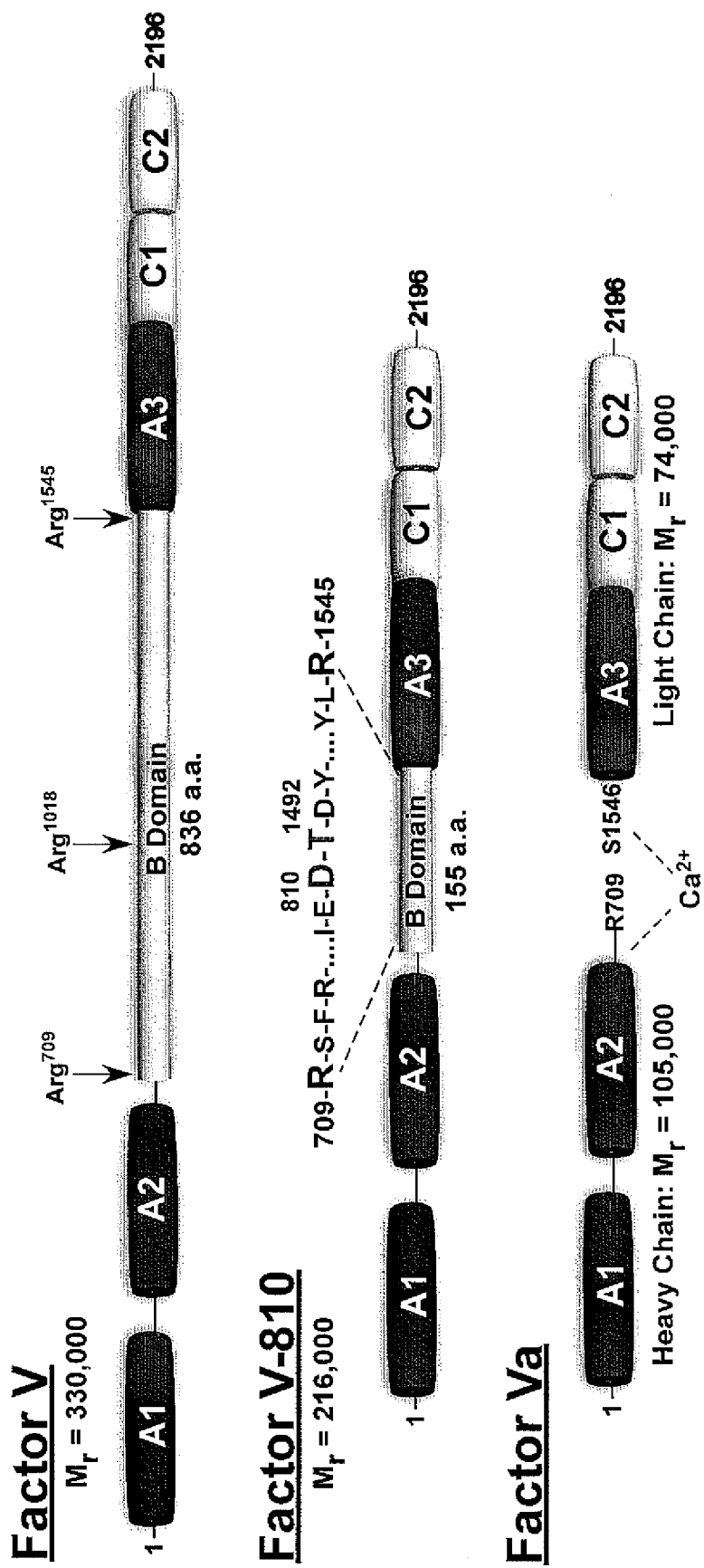
FIG. 5 Schematic representation of FV, FV-810 and FVa. The sequence above FV-810 indicates which B-domain elements have been deleted. IIa cleavage sites are indicated as well as the molecular weight of the various fragments.

In addition to using activated factor V (FVa), we have engineered single chain FV derivatives in which large segments of the B-domain have been deleted (For example, $FVdes^{811-1491}$; FV-810, Journal of Biological Chemistry, (2004) 279: 21643-21650; FIG. 5). We have also made additional derivatives which have cofactor-like properties as well. For example, FV-902 (factor V des903-1491) also has activity profiles that are similar to FV-810 and the activated form of FV. These B-domain truncated derivatives exhibit functional proprieties equivalent to FVa, even in the absence of intentional proteolysis. The usefulness of these derivatives in the context of this application are: 1) they are secreted from the mammalian cell line in a single-chain form, and do not require intentional proteolytic activation with thrombin or factor Xa; 2) they have activities that are comparable to two-chain active factor Va; 3) they do not need to be further processed with thrombin; and 4) they may be more stable in plasma compared to two-chain factor Va (i.e have better half-lives).

Additional Useful Derivatives Include:
FV-810; factor V lacking amino acids 811-1491; (published JBC, 279, 2004, 21643-21650)
FV-859; factor V lacking amino acids 860-1491;
FV-866; factor V lacking amino acids 867-1491;
FV-902; factor V lacking amino acids 903-1491;

FV-924; factor V lacking amino acids 923-1491;
FV-937; factor V lacking amino acids 938-1491;
FV-956; factor V lacking amino acids 957-1491;
Others Include:
FV-1033-B58-s131; factor V lacking amino acids 1034-1491 with amino acids 900-1030 exchanged with amino acids 907-1037 of factor VIII;
FV-1033-B58-s104; factor V lacking amino acids 1034-1491 with amino acids 904-1007 exchanged with amino acids 972-1075 of factor VIII;
FV-1033-B58-s46; factor V lacking amino acids 1034-1491 with amino acids 963-1008 exchanged with amino acids 1032-1077 of factor VIII;
Each of the above derivatives exhibit functional properties which are comparable to two chain the activated form of FV.

In order to enhance stability of the molecules in vivo and provide resistance or protection the protein C pathway each of the above derivatives could be modified at:

Arg506
Arg306
Arg679

While in theory any amino acid could be exchanged at this site, Gln is preferable.

Thus, the methods and compositions of the invention could be used to treat patients with hemophilia A and hemophilia B; patients with hemophilia A and B who have inhibitory antibodies to either factor VIII or factor IX, respectively; and other hemostatic disorders.

I. DEFINITIONS

Various terms relating to the biological molecules of the present invention are used hereinabove and also throughout the specification and claims.

The phrase "activated form of FV" refers to a modified form of FV which has been genetically altered such that it exhibits cofactor activity comparable to two-chain FVa in the absence of intentional proteolysis and in the absence of specific cofactors. Preferred sites for amino acid alterations in the parent FV molecule are described above.

The phrase "hemostasis related disorder" refers to bleeding disorders such as hemophilia A and B, hemophilia A and B patients with inhibitory antibodies, deficiencies in coagulation Factors, VII, IX and X, XI, V, XII, II, von Willebrand factor, combined FV/FVIII deficiency, vitamin K epoxide reductase C1 deficiency, gamma-carboxylase deficiency; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5 or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (at http://www.ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

II. PREPARATION OF ACTIVATED FORMS OF FV ENCODING NUCLEIC ACID MOLECULES, POLYPEPTIDES AND DERIVATIVES THEREOF

A. Nucleic Acid Molecules

Nucleic acid molecules encoding the activated forms of FV or derivative thereof of the invention may be prepared by using recombinant DNA technology methods. The availability of nucleotide sequence information enables preparation of isolated nucleic acid molecules of the invention by a variety of means. For example, nucleic acid sequences encoding the activated forms of FV or derivative thereof polypeptide may be isolated from appropriate biological sources using standard protocols well known in the art.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Alternatively, the nucleic acids may be maintained in vector suitable for expression in mammalian cells. In cases where post-translational modification affects the activated forms of FV or derivative thereof function, it is preferable to express the molecule in mammalian cells.

The activated forms of FV or derivative thereof-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting the activated form of FV expression.

B. Proteins

A full-length activated form of FV or derivative thereof polypeptide of the present invention may be prepared in a variety of ways, according to known methods. The protein may be purified from appropriate sources, e.g., transformed bacterial or animal cultured cells or tissues which express the activated form of FV, by immunoaffinity purification. However, this is not a preferred method due to the low amount of protein likely to be present in a given cell type at any time.

The availability of nucleic acid molecules encoding an activated form of FV or derivative thereof polypeptide enables production of the activated form of FV or derivative thereof using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of the activated form of FV or derivative thereof may be produced by expression in a suitable prokaryotic or eukaryotic expression system. For example, part or all of a DNA molecule encoding the activated form of FV for example, may be inserted into a plasmid vector adapted for expression in a bacterial cell, such as E. coli or a mammalian cell such as CHO or Hela cells. Alternatively, in a preferred embodiment, tagged fusion proteins comprising the activated form of FV or derivative thereof can be generated. Such activated form of FV or derivative thereof-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as E. coli or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

The activated form of FV or derivative thereof proteins, produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

The activated form of FV or derivative thereof proteins, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as reticulocyte lysate.

III. USES OF THE ACTIVATED FORM OF FV OR DERIVATIVE THEREOF—ENCODING NUCLEIC ACIDS AND PROTEINS

The activated form of FV polypeptide or derivative thereof or nucleic acids encoding the same having altered coagulation activities may be used according to this invention, for example, as therapeutic and/or prophylactic agents which modulate the blood coagulation cascade. The present inventors have discovered that these molecules can be altered to increase coagulation.

A. In a preferred embodiment of the present invention, the activated form of FV or derivative thereof may be administered to a patient via infusion in a biologically compatible carrier, preferably via intravenous injection. The activated form of FV or derivative thereof of the invention may optionally be encapsulated into liposomes or mixed with other phospholipids or micelles to increase stability of the molecule. The activated form of FV or derivative thereof may be administered alone or in combination with other agents known to modulate hemostasis (e.g., Factor VIIa, FIX, FVIII or FX/Xa and derivatives thereof). An appropriate composition in which to deliver the activated form of FV or derivative thereof may be determined by a medical practitioner upon consideration of a variety of physiological variables, including, but not limited to, the patient's condition and hemodynamic state. A variety of compositions well suited for different applications and routes of administration are well known in the art and are described hereinbelow.

The preparation containing the purified activated forms of FV or derivative thereof contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the factor V/Va analog can be stored in the form of a finished solution or in lyophilized or deep-frozen form. Preferably the preparation is stored in lyophilized form and is dissolved into a visually clear solution using an appropriate reconstitution solution.

Alternatively, the preparation according to the present invention can also be made available as a liquid preparation or as a liquid that is deep-frozen.

The preparation according to the present invention is especially stable, i.e., it can be allowed to stand in dissolved form for a prolonged time prior to application.

The preparation according to the present invention can be made available as a pharmaceutical preparation with the activated form of FV or derivative thereof in the form of a one-component preparation or in combination with other factors in the form of a multi-component preparation.

Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, preferably using a method, such as is described in EP 0 714 987.

Another feature of this invention relates to making available a preparation which contains an activated form of FV or derivative thereof with a high stability and structural integrity and which, in particular, is free from inactive factor V/Va analog intermediates and autoproteolytic degradation products and which can be produced by activating a factor V analog of the type described above and by formulating it into an appropriate preparation.

The pharmaceutical preparation may contain dosages of between 10-1000 µg/kg, more preferably between about 10-250 µg/kg and most preferably between 10 and 75 µg/kg, with 40 µg/kg of the variant factor V polypeptide being particularly preferred. Patients may be treated immediately upon presentation at the clinic with a bleed. Alternatively, patients may receive a bolus infusion every one to three hours, or if sufficient improvement is observed, a once daily infusion of the activated form of FV or derivative thereof described herein.

B. The Activated Form of FV or Derivative Thereof or Derivative Thereof-Encoding Nucleic Acids The activated form of FV or derivative thereof-encoding nucleic acids may be used for a variety of purposes in accordance with the present invention. In a preferred embodiment of the invention, a nucleic acid delivery vehicle (i.e., an expression vector) for modulating blood coagulation is provided wherein the expression vector comprises a nucleic acid sequence coding the activated form of FV or derivative thereof polypeptide, or a functional fragment thereof as described herein. Administration of the activated form of FV or derivative thereof-encoding expression vectors to a patient, results in the expression of the activated form of FV or derivative thereof polypeptide which serves to enhance coagulation. In accordance with the present invention, the activated form of FV or derivative thereof encoding nucleic acid sequence may encode the activated form of FV or derivative thereof polypeptide as described herein whose expression modulates hemostasis.

Expression vectors comprising the activated form of FV or derivative thereof nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible composition.

In a preferred embodiment of the invention, the expression vector comprising nucleic acid sequences encoding the activated form of FV or derivative thereof is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-2, AAV-5, AAV-7, and AAV-8) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, and retroviral vectors.

In a preferred embodiment of the present invention, methods are provided for the administration of a viral vector comprising nucleic acid sequences encoding an activated form of FV or derivative thereof, or a functional fragment thereof. Adenoviral vectors of utility in the methods of the present invention preferably include at least the essential parts of adenoviral vector DNA. As described herein, expression of the activated form of FV or derivative thereof polypeptide following administration of such an adenoviral vector serves to modulate hemostasis.

Recombinant adenoviral vectors have found broad utility for a variety of gene therapy applications. Their utility for such applications is due largely to the high efficiency of in vivo gene transfer achieved in a variety of organ contexts.

Adenoviral particles may be used to advantage as vehicles for adequate gene delivery. Such virions possess a number of desirable features for such applications, including: structural features related to being a double stranded DNA nonenveloped virus and biological features such as a tropism for the human respiratory system and gastrointestinal tract. Moreover, adenoviruses are known to infect a wide variety of cell types in vivo and in vitro by receptor-mediated endocytosis. Attesting to the overall safety of adenoviral vectors, infection with adenovirus leads to a minimal disease state in humans comprising mild flu-like symptoms.

Due to their large size (~36 kilobases), adenoviral genomes are well suited for use as gene therapy vehicles because they can accommodate the insertion of foreign DNA following the removal of adenoviral genes essential for replication and nonessential regions. Such substitutions render the viral vector impaired with regard to replicative functions and infectivity. Of note, adenoviruses have been used as vectors for gene therapy and for expression of heterologous genes.

For a more detailed discussion of the use of adenovirus vectors utilized for gene therapy, see Berkner, 1988, Biotechniques 6:616-629 and Trapnell, 1993, Advanced Drug Delivery Reviews 12:185-199.

It is desirable to introduce a vector that can provide, for example, multiple copies of a desired gene and hence greater amounts of the product of that gene. Improved adenoviral vectors and methods for producing these vectors have been described in detail in a number of references, patents, and patent applications, including: Mitani and Kubo (2002, Curr Gene Ther. 2(2); 135-44); Olmsted-Davis et al. (2002, Hum Gene Ther. 13(11): 1337-47); Reynolds et al. (2001, Nat. Biotechnol. 19(9):838-42); U.S. Pat. Nos. 5,998,205 (wherein tumor-specific replicating vectors comprising multiple DNA copies are provided); 6,228,646 (wherein helper-free, totally defective adenovirus vectors are described); 6,093,699 (wherein vectors and methods for gene therapy are provided); 6,100,242 (wherein a transgene-inserted replication defective adenovirus vector was used effectively in in vivo gene therapy of peripheral vascular disease and heart disease); and International Patent Application Nos. WO 94/17810 and WO 94/23744.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of the activated form of FV or derivative thereof or functional fragments thereof. For example, an E1 deleted type 5 adenoviral vector comprising nucleic acid sequences encoding the activated form of FV or derivative thereof under the control of a cytomegalovirus (CMV) promoter may be used to advantage in the methods of the present invention.

Exemplary Methods for Producing Adenoviral Vectors

Adenoviral vectors for recombinant gene expression have been produced in the human embryonic kidney cell line 293 (Graham et al., 1977, J. Gen. Virol. 36:59-72). This cell line is permissive for growth of adenovirus 2 (Ad2) and adenovirus 5 mutants defective in E1 functions because it comprises the left end of the adenovirus 5 genome and, therefore, expresses E1 proteins. E1 genes integrated into the cellular genome of 293 cells are expressed at levels which facilitate the use of these cells as an expression system in which to amplify viral vectors from which these genes have been deleted. 293 cells have been used extensively for the isolation and propagation of E1 mutants, for helper-independent cloning, and for expression of adenovirus vectors. Expression systems such as the 293 cell line, therefore, provide essential viral functions in trans and thereby enable propagation of viral vectors in which exogenous nucleic acid sequences have been substituted for E1 genes. See Young et al. in The Adenoviruses, Ginsberg, ed., Plenum Press, New York and London (1984), pp. 125-172.

Other expression systems well suited to the propagation of adenoviral vectors are known to those of skill in the art (e.g., HeLa cells) and have been reviewed elsewhere.

Also included in the present invention is a method for modulating hemostasis comprising providing cells of an individual with a nucleic acid delivery vehicle encoding the activated form of FV or derivative thereof polypeptide and allowing the cells to grow under conditions wherein the activated form of FV or derivative thereof polypeptide is expressed.

From the foregoing discussion, it can be seen that the activated form of FV or derivative thereof polypeptide or nucleic acids encoding the same may be used in the treatment of disorders associated with aberrant blood coagulation.

C. Pharmaceutical Compositions

The expression vectors of the present invention may be incorporated into pharmaceutical compositions that may be delivered to a subject, so as to allow production of a biologically active protein (e.g., the activated form of FV or derivative thereof polypeptide or functional fragment or derivative thereof). In a particular embodiment of the present invention, pharmaceutical compositions comprising sufficient genetic material to enable a recipient to produce a therapeutically effective amount of the activated form of FV or derivative thereof polypeptide can influence hemostasis in the subject. Alternatively, as discussed above, an effective amount of the variant Factor V polypeptide may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents which influence hemostasis.

In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art. The pharmaceutical compositions of the present invention may be manufactured in any manner known in the art (e.g., by means of conventional mixing, dissolving, granulating, dragee-making, levigating, emulsifying, encapsulating, entrapping, or lyophilizing processes).

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, which is combined with buffer prior to use.

After pharmaceutical compositions have been prepared, they may be placed in an appropriate container and labeled for treatment. For administration of the activated form of FV or derivative thereof-containing vectors, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques provided in the present invention. Therapeutic doses will depend on, among other factors, the age and general condition of the subject, the severity of the aberrant blood coagulation phenotype, and the strength of the control sequences regulating the expression levels of the activated form of FV or derivative thereof polypeptide. Thus, a therapeutically effective amount in humans will fall in a relatively broad range that may be determined by a medical practitioner based on the response of an individual patient to vector-based activated form of FV or derivative thereof treatment.

D. Administration

The variant activated form of FV polypeptides, alone or in combination with other agents may be directly infused into a patient in an appropriate biological carrier as described hereinabove. Expression vectors of the present invention comprising nucleic acid sequences encoding the activated form of FV or derivative thereof, or functional fragments thereof, may be administered to a patient by a variety of means (see below) to achieve and maintain a prophylactically and/or therapeutically effective level of the activated form of FV or derivative thereof polypeptide. One of skill in the art could readily determine specific protocols for using the activated form of FV or derivative thereof encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety.

The activated form of FV or derivative thereof encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720, 720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising the activated form of FV or derivative thereof nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding the activated form of FV or derivative thereof polypeptide.

Also provided are lentivirus or pseudo-typed lentivirus vectors comprising a nucleic acid sequence encoding an activated form of FV or derivative thereof polypeptide Also encompassed are naked plasmid or expression vectors comprising a nucleic acid sequence encoding an activated form of FV or derivative thereof polypeptide.

The Example set forth below is provided to illustrate certain embodiments of the invention. It is not intended to limit the invention in any way.

Example I

The following materials and methods are provided to facilitate the practice of the present invention.

Animals

The local Animal Care and Use Committee approved all procedures. Murine models for severe FVIII [20] or FIX deficiency [21] were crossed with mice carrying FVL (on C57B16 background) generated by knock-in technology as previously described [22, 23]. The hemophilia B model was generated on a C57B1/6-129 mixed background [21, 24] and further crossed into C57B1/6 for additional five generations. The hemophilia A mice were on C57B1/6-129 mixed background. Through a series of breedings we obtained hemophilia A or B mice of all three expected FVL genotypes, which allow comparison littermate mice.

Coagulation Assays

Blood samples obtained by tail clipping were collected into 3.8% sodium citrate (9 parts of blood: 1 part anticoagulant). Clotting factor activity was determined by a modified one stage assay incubating 50 µl of human FIX- or FVIII-deficient plasma with 50 µl of automated activated partial thromboplastin time (aPTT) reagent (Organon Teknika, Durham, N.C.), and a total of 50 µl of undiluted test sample. Fifty microliters of 25 mM $CaCl_2$ were added, and time to clot formation was measured using Stat4 Coagulation Instrument (Diagnostic Stago, Parsipanny, N.J.). Thrombin-antithrombin (TAT) complexes were measured by Enzygnost TAT enzyme-linked immunosorbent assay (ELISA) purchased from Dade Behring (Marburg, Germany), as previously described, which present high cross reactivity with murine TAT [25, 26].

Tail Clipping Assay

Mice were anesthetized and the distal portion of the tail (2.5-3 mm of diameter) was cut and immersed in 37° C. saline solution. Bleeding time measurements exceeding 10 min were stopped by suture of the tail. The blood loss was determined by measuring the absorbance of hemoglobin ($A_{575}$ nm) in the saline solution in which the tail was placed, as reported [26].

Ferric Chloride ($FeCl_3$) Carotid Artery Model

The carotid artery of adult mice was exposed, a Doppler flow probe (Model 0.5VB; Transonic Machinery Systems, Ithaca, N.Y.) was placed on the surface of the exposed artery and a baseline blood flow measurement recorded. Subsequently, a 2 $mm^2$ piece of Whatman #1 paper soaked in ferric chloride (15% solution) was applied to the adventitial surface of the exposed artery for 2 minutes, after which it was removed, and carotid artery blood flow recorded. Time to carotid artery occlusion was defined as the time after initiation of arterial injury and the onset of stable occlusion[27].

Real-Time Widefield Intravital Microscope

The cremaster muscle of adult mice was exposed, stretched and pinned across the intravital microscopy tray. The rat anti-CD41 (murine platelet glycoprotein complex IIb/IIIa) Alexa-555 labeled antibody (Molecular Probes, Eugene, Oreg.) was infused at a dose of 10 µg per mouse. Immediately after infusion of the antibody, a laser-induced injury was performed on the vessel wall of the cremasteric arterioles [28]. The injuries were performed using a pulse-nitrogen dye laser applied through the micropoint laser system (Phototonic Instruments St. Charles, Ill.). We used an Olympus BX6IWI fixed-stage motorized upright fluorescence microscope with a long-distance condenser and 40× water-immersion objective. Data analysis was carried out utilizing the Slidebook 4.0 software (Intelligent Imaging Innovations, Denver, Colo.). Fluorescence data were captured digitally up to 10 milliseconds/event for 300 frames. The amount of platelet accumulation in the developing thrombi was determined by the sum of all pixel values of the platelet-specific signal and expressed as relative fluorescence unit (RFU), an arbitrary unit in which the integrated platelet fluorescence intensity is determined.

Assessing Effects of FV or FVa Proteins in the Hemostasis of Hemophilia Mice.

Human FV was isolated from plasma and recombinant FVa was prepared as described before [29]. Purification of both proteins was carried out using an immunoaffinity column containing anti-human F.V antibody [29]. For in vitro activation of FV, 20 nM FV was incubated with murine or human thrombin (Haematological Technologies, Inc. Essex-Junction, Vt.) at concentration of 0.25 nM at 37° C. Samples were withdrawn from the reaction mixtures at several time points and the specific cofactor activity was determined by a PT-based assay using FV-deficient plasma. To determine the cleavage of FV by murine or human thrombin, 300 nM of single chain FV was incubated for several time intervals with thrombin (1 nM). Samples were removed and analyzed by SDS-PAGE. Next, FVa was infused via the tail vein into hemophilia B mice and blood samples were collected by tail clipping prior to protein infusion, and after 15 and 120 minutes for determination of FVa levels, aPTTs, and TAT levels. Next, we injected human FVa (30-60 µg/mouse) or FV (60-120 µg/mouse) through the jugular vein of hemophilia A or B mice and monitored clot formation in the intravital microscopy over a period of two hours.

Statistical Analysis

Comparison of data obtained from distinct experimental groups was analyzed using JMP version 4.0.2 (SAS Institute Inc. Cary, N.C.).

Results

Hemophilia A and B Mice with FVL Present Improved Clotting Times

The determination of clotting activity for hemophilia A mice homozygous or heterozygous for FVL mutation revealed shortening of the aPTT values when compared to hemophilia A mice without FVL (FIG. 1A). Similar improvement on the aPTT values was also determined for hemophilia B mice with FVL (FIG. 1B). We next determined TAT levels, to verify whether the improvement of the aPTT values was associated with increased thrombin generation. This immunoassay was developed to detect human TAT but also presents high cross-reactivity to murine TAT [25,26]. There was a good correlation between shortening of the aPTT and increased levels of TAT (FIG. 1, panels C and D). However, TAT levels of hemophilia mice with FVL did not reach those of FVL without hemophilia (FIG. 1, panel F).

Blood Loss Following Tail-Clipping is Reduced Among Hemophilia B Mice Carrying FVL.

Figure 2:
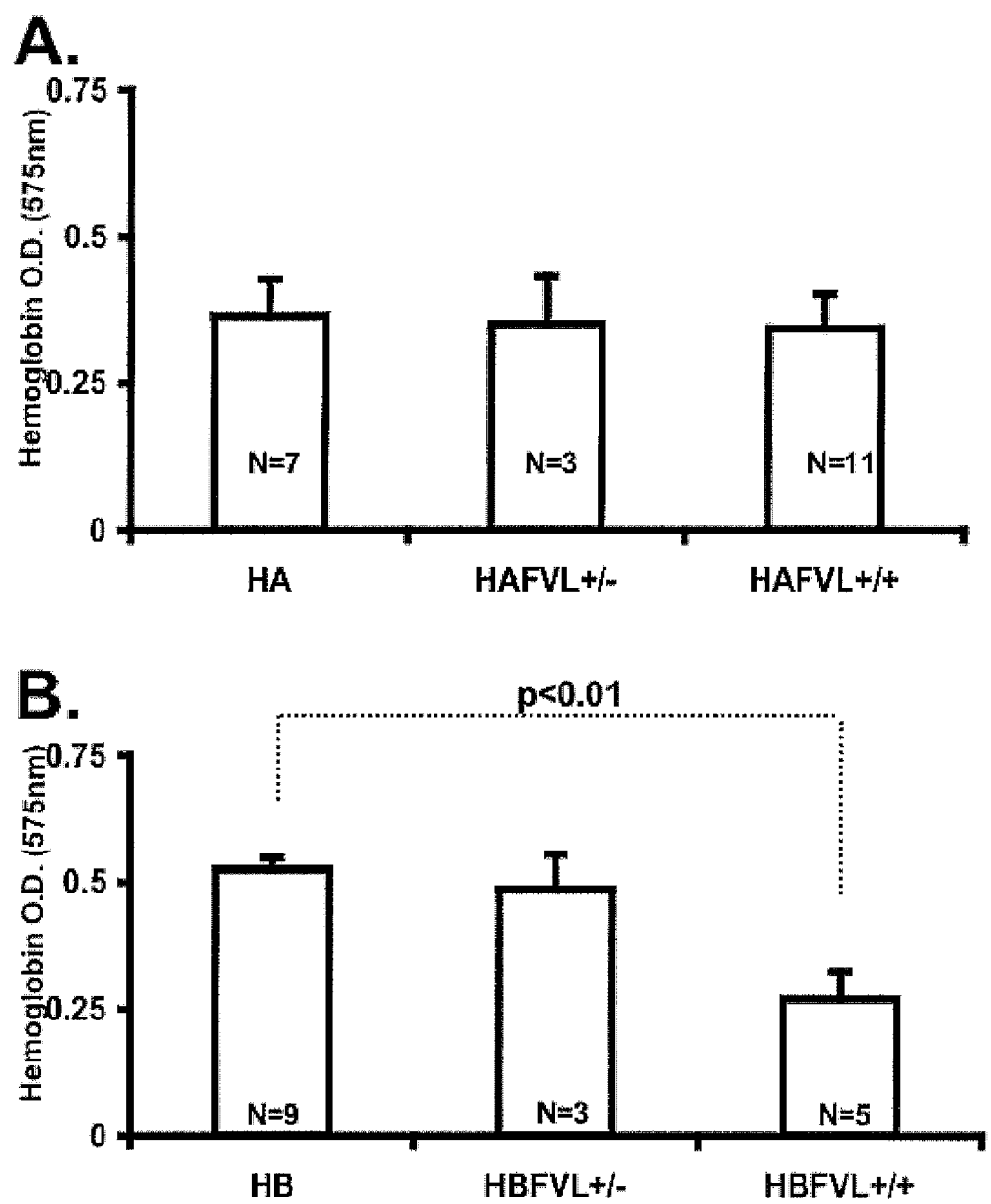
FIG. 2. Hemostatic assessment following tail clip assay in hemophilic mice crossed with Factor V Leiden (FVL). Blood loss was measured by hemoglobin content of the saline solution by optical density at $A_{575}$ post tail clipping of hemophilia mice. Panel A: Hemophilia A (HA) mice, HA heterozygous (+/−) and homozygous for FVL (+/+) were compared. Panel B: Littermates hemophilia B (HB), HB heterozygous (+/−) and homozygous for FVL (+/+) were compared. The numbers of animals per group are indicated. P value was calculated by t-test.

We next tested whether the mild improvement of the clotting times in vitro was associated with in vivo hemostatic performance. Blood loss was measured during a ten minute period after sectioning the distal part of the tail. No difference was seen among hemophilia A with or without FVL (FIG. 2A), whereas the blood loss among hemophilia B mice homozygous for FVL was reduced when compared with mice without the mutation (FIG. 2B).

No Sustained Thrombus Formation Following Carotid Artery Injury in Hemophilia Mice with FVL.

All normal mice (n=5) or FVL homozygous mice (n=5) tested without hemophilia presented full vessel occlusion (Table 1), which was characterized by the interruption of blood flow within 6 to 8 min post vessel injury. In contrast, no vessel occlusion was detected in hemophilia A mice without FVL (Table 1). In two out of ten hemophilia A mice with FVL, only a transient reduction of the blood flow was detected, but not at the levels to suggest full lumen occlusion (Table 1). Similar findings were determined among hemophilia B homozygous for FVL, with only one of the eight mice developing a complete and one a transient vessel occlusion.

TABLE 1

Carotid artery occlusion following FeCl$_3$-induced injury model.

| Genotype | N. of mice | N. of mice with occlusion | | Occlusion time ± SD |
|---|---|---|---|---|
| | | Transient | Complete | |
| WT | 5 | 0 | 5 | 6.3 ± 2 min |
| FVL (+/+) | 5 | 0 | 5 | 6.5 ± 1 min |
| HA | 5 | 0 | 0 | — |
| HA/FVL (+/−) | 5 | 1 | 0 | — |
| HA/FVL (+/+) | 5 | 1 | 0 | — |
| HB | 5 | 0 | 0 | — |
| HB/FVL (+/−) | 4 | 0 | 0 | — |
| HB/FVL (+/+) | 8 | 1 | 1 | 6 min |

WT: wild-type controls; FVL: Factor V Leiden; HA: hemophilia A; HB: hemophilia B.

Figure 3:
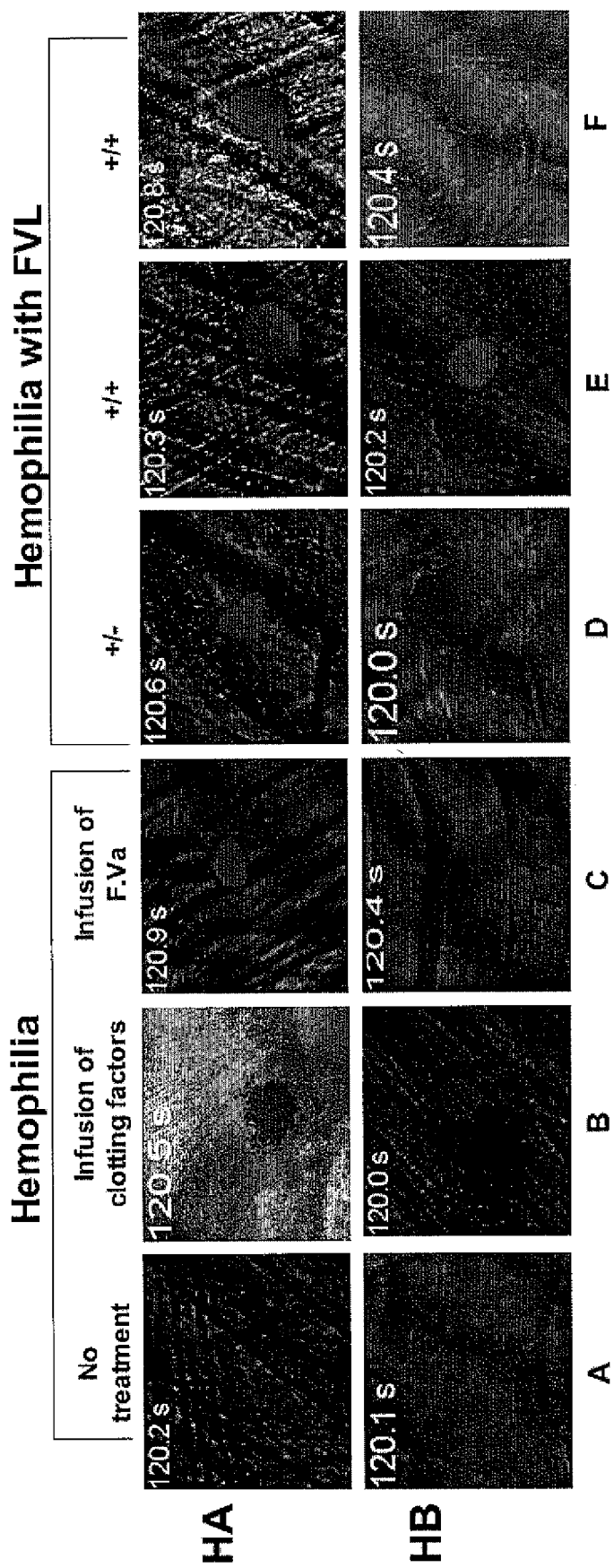
FIG. 3. Platelet deposition in arterial thrombi in mice upon laser-induced endothelial damage using fluorescence signals. Upper panels represent data from hemophilia A (HA) mice and bottom panels are data from hemophilia B (HB) mice. Platelet deposition was monitored using an anti-CD41 Alexa-555 labeled antibody and composite images at ~120 seconds post laser injury are shown. Thrombus formation was assessed at the baseline (panel A) and after protein replacement (panel B). Hemophilic mice homozygous or heterozygous for FVL are shown in panels D to F. Hemophilic mice injected with 30 μg of FVa (Panel C).

FVL Restores the Ability to Form Thrombi in Hemophilic Mice at the Microcirculation Level We monitored platelet accumulation during real-time imaging of the laser-induced endothelial damage in the microcirculation. The composite image consisted of a brightfield image of the thrombus and fluorescence image of platelets (FIG. 3). In normal mice (n=3), we determined that all injured arteriole sites (n=30) resulted in clot formation. In addition, we characterized the thrombus formation of FVL homozygous mice (n=4), and as expected, clots formed in all (n=40) injured sites (Table 2).

TABLE 2

Summary of thrombus formation following laser-induced endothelial damage.

| Genotype | N. of mice | N. of sites injured | N. of clots (%) |
|---|---|---|---|
| WT | 3 | 30 | 30 (100) |
| FVL | 4 | 40 | 40 (100) |
| Hemophilia A | | | |
| FVL (+/+) | 5 | 45 | 45 (100) |
| FVL (+/−) | 6 | 43 | 43 (100) |
| FVL (−/−) | 8 | 39 | 0* |
| F.VIII infusion | 3 | 8 | 8 (100) |
| Hemophilia B | | | |
| FVL (+/+) | 4 | 40 | 40 (100) |
| FVL (+/−) | 3 | 18 | 18 (100) |
| FVL (−/−) | 4 | 16 | 0* |
| F.IX infusion | 3 | 21 | 21 (100) |
| Infusion of FVa | | | |
| Hemophilia A | 2 | 8 | 8 (100) |
| Hemophilia B | 2 | 13 | 13 (100) |
| Infusion of FV | | | |
| Hemophilia A | 2 | 10 | 0* |
| Hemophilia B | 2 | 11 | 0 |

WT: wild-type controls; FVL: Factor V Leiden; (+) Denotes presence of FVL mutation. For infusion experiments, purified F.IX (Monomine, Aventis Behring, Kankakee, IL) and recombinant F.VIII (Kogenate FS, Bayer, West Haven, CT) were used.
*Fischer's exact test was used for statistical analysis comparison between hemophilic mice with and without FVL (P < 0.001) or mice infused with FV and FVa (P < 0.001).

In contrast, no thrombus formation was detected in mice with hemophilia A (n=8) or B (n=4) following successive vascular injuries to a total of 68 injury sites, averaging 3-10 sites per mouse (FIG. 3, panel A; Table 2). However, when these animals received intravenous injection of human purified FVIII or FIX concentrates at doses to achieve ~100% of normal levels, clots formed in all injury sites (FIG. 3, panel B).

Figure 4:
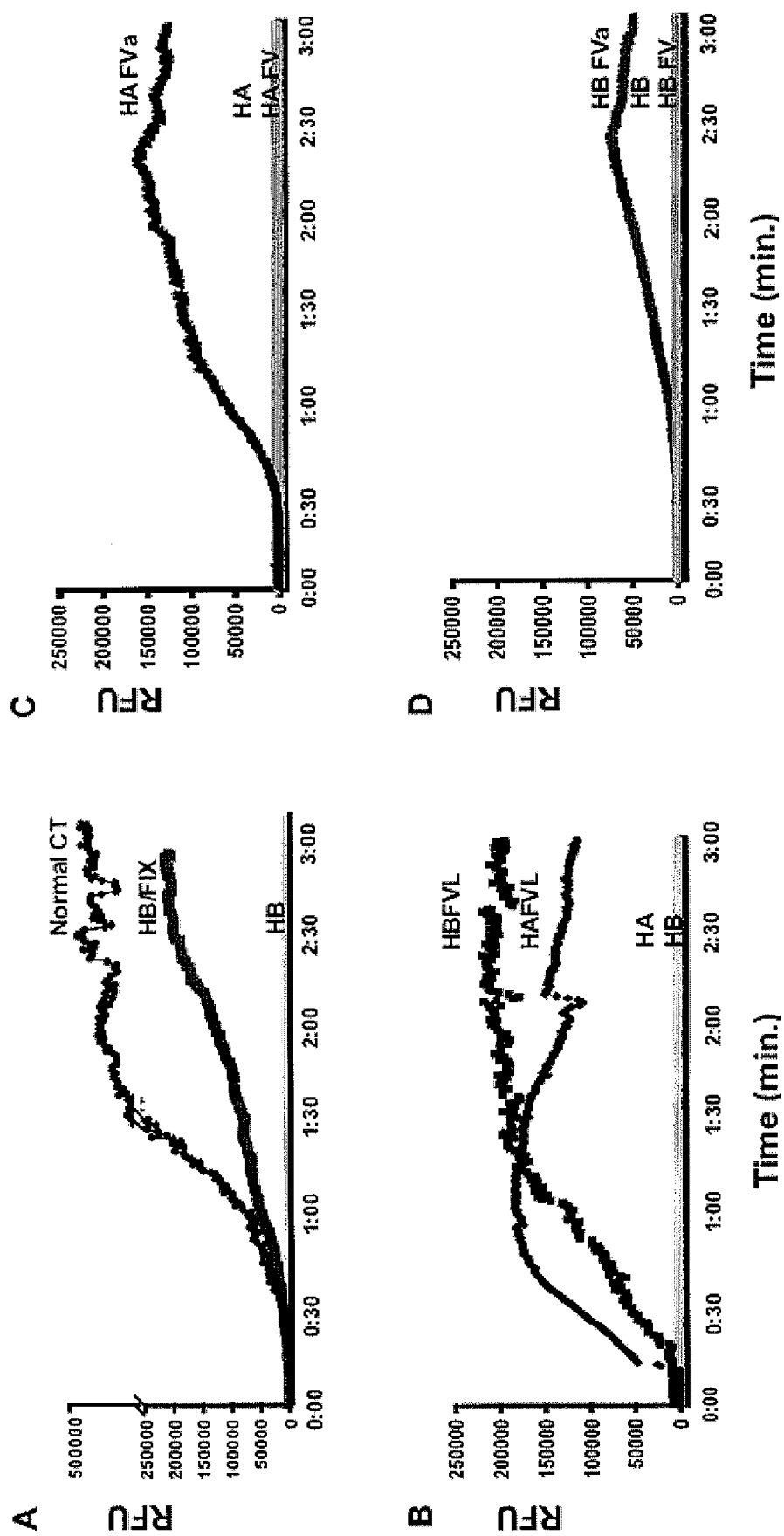
FIG. 4. Time course of platelet accumulation in arterial thrombi. Platelet deposition in developing thrombin over time was monitored with anti-CD41 Alexa-55 labeled antibody. The arbitrary relative fluorescent unit (RFU) represents the median platelet-derived fluorescence for several thrombi. Panel A represents hemophilia B mice (HB), HB mice infused with human F.IX concentrated and hemostatically normal C57B1/6 mice as control (CT). Panel B represents hemophilia A (HA) or KB mice homozygous for Factor V Leiden (FVL) and naïve hemophilic mice. Panels C and D represents hemophilia A (HA) or (HB) naïve mice or injected with purified FV or FVa proteins. These experiments are representative of multiple thrombi (>5 thrombi/mouse) in (2-4) mice per group, as shown in table 2.

We next tested hemophilia A (n=5) or B mice (n=4) homozygous for FVL. Clot formation was observed in all 85 injured sites (ranging from 5-10 sites/mouse) and remained stable for the duration of the experiment Wig. 3 panels E and F). Interestingly, similar results were obtained in hemophilia A (n=6) or hemophilia B (n=3) mice heterozygous for FVL. In this group, a total of 61 injury sites were analyzed and thrombus formation was consistently detected (FIG. 3, panel D). Time course of platelet deposition is shown in FIG. 4 for groups of hemophilic mice. The data is represented by the median values of RFU derived from the platelet deposition, which represent a relative comparison among different groups tested. There was a increase in platelet deposition over time for both hemophilia models with FVL as compared to hemophilia mice without the mutation (FIG. 4, panel B).

Infusion of Purified FVa Induces Thrombus Formation in Murine Models of Hemophilia A or B Initially we have determined that murine thrombin activates human FV in a similar fashion to human thrombin. To test if transient increment in the FV or FVa levels could mimic the in vivo effect of FVL, we injected mice with purified human FV or FVa. Because FVa is secreted in the active form, there is no requirement for thrombin activation of the purified protein [29]. Therefore, direct interpretation of these data is not confounded by traces of thrombin in the protein solution infused. Infusion of 30 μg of FVa/mouse into hemophilia B mice resulted in discrete shortening of the aPTT from 77±3 seconds at baseline to 72±4 seconds at both time points (15 or 120 minutes) post infusion. These data were in good agreement with increased levels of TAT from 15±5 ng/ml (at baseline) to 69±10 and 67±22 ng/ml at 15 and 120 minutes, respectively. We next monitored clot formation in the intravital microscopy. Prior to the protein infusion, no clot formation was observed in both hemophilia A and B mice, as expected. Following infusion of 30 μg or 100 μg of FVa, platelet accumulation was readily observed at all injury sites (FIG. 4, panel C and D). In contrast, when mice were injected with the procofactor FV at comparable doses to achieve similar plasma concentration (0.180 or 0.360 pmoles), no clot formation was detected. Collectively these results were similar for both hemophilia models (Table 2 and FIG. 4, panels C-D).

Discussion

The assessment of the clinical impact of FVL on the hemophilia phenotype has been controversial and hampered by the complex interaction of other acquired and genetic modifying factors. Therefore, the use of murine models minimizes the influence of several acquired factors. The occurrence of spontaneous bleeding episodes in murine models for severe hemophilia A or B is rare. Thus, to properly address the effect of FVL on the severe hemophilia phenotype, a series of in vivo hemostatic tests were imposed upon these animal models.

Hemophilia mice with FVL mutation presented improvement in hemostasis, as determined by shortening of the aPTT-based assays and increased TAT levels, which reflects enhanced thrombin generation. To address whether improvement on in vitro parameters of hemostasis had any relevant impact on the hemophilia phenotype in vivo, mice underwent a series of hemostatic challenges.

In one model a mechanical injury was induced by transfection of the tail vessels; in a second, the injury was induced by a ferric chloride chemical to the carotid artery. The latter model is characterized by oxidative injury that disrupts the endothelium and exposes the subendothelium [30]. Hemophilia B mice homozygous for FVL presented modest improvement of hemostasis in both methods when compared with littermates without FVL whereas among hemophilia A models no improvement was found. It is possible that differences in mouse strains may affect some of the hemostatic parameters, as already shown for FVL [22]. These data suggest that, upon injury of large vessels, FVL does not provide a major beneficial hemostatic effect.

The real-time imaging of thrombus formation developed by Furie and colleagues [28], in conjunction with the laser-induced endothelial injury model [31], provides a sensitive method for evaluation of hemostasis at the microcirculation of a living animal. It has been observed that the outcome of this method is not full occlusion of the vessel lumen; rather, endothelial cells appear to be activated instead of disrupted with less exposure of the subendothelium [28, 31]. In hemophilia mice with no FVL mutation, no clot was observed even upon successive laser expositions. However, following replacement of the missing clotting factor by intravenous infusion of human FVIII or FIX concentrates, clot formation was observed in all arteriole sites injured. Hemophilia A or B mice homozygous for the FVL mutation have restored ability to form a thrombus. Interestingly, among hemophilia mice heterozygous for FVL, thrombus formation is comparable to homozygous FVL. This is particularly interesting since most human subjects with hemophilia and FVL carried only one FVL allele.

When extrapolating data from murine models to humans it is important to consider the differences between human and murine FV such the origin of FV synthesis [32, 33] and differences in the APC pathway such as the ability of human aPC to properly inactivate murine FVa [34], and the absence of the plasma protein C inhibitor [35]. To better assess the role of the APC pathway as a modifier of the hemophilia phenotype, other components such as thrombomodulin or endothelial protein C receptor (EPCR) functions [36] need to be investigated. The vascular distribution of thrombomodulin and EPCR differs as a function of vessel size. The results of murine models are informative because improvements in hemostasis by FVL seem to be vessel-dependent (i.e. micro vs. macro circulation). Thrombomodulin concentration in the microcirculation is >1000-fold higher than in vessels of ~0.3 cm diameter, which facilitates binding to thrombin and consequently clotting activity is depressed. We speculate that in the presence of FVL, the continuous thrombin generation at the microcirculation may lead to high free thrombin; therefore, the coagulation is locally enhanced. In large vessels, such as the murine carotid artery (diameter of ~0.55 mm), thrombin is likely free since thrombomodulin levels are relatively low [37, 38]. Therefore, the impact of the FVL is not sufficient to significantly alter hemostasis at the macrocirculation level.

Using human hemophilia A plasma, Mann and colleagues demonstrated that slow formation of FVa is an additional factor that impacts the impaired thrombin generation. Because free FXa is rapidly inactivated, the presence of fully active FVa complexed with FXa in the prothrombinase complex is critical to prevent FXa inactivation by antithrombin and tissue factor pathway inhibitors [39]. Further experiments showed that increasing FV levels up to 150% in hemophilia A plasma did not result in significant enhancement of thrombin, whereas adding FVL to levels of 100% or 150% enhanced thrombin generation by 3 and 5-fold, respectively [1,5]. Recently, a similar effect was determined in hemophilia B plasma [1,6]. Therefore, we hypothesized that an increase in FVa levels could mimic the effect of FVL in hemophilia mice. The results demonstrated that FVa, but not FV, has the ability of restoring the hemophilia phenotype at the microcirculation level, in a similar manner as findings indicate that FVL does.

There is evidence that in humans FV, but not FVL, presents cofactor activity in the APC-mediated inactivation of FVIIIa. Recently, Simioni et al demonstrated increased thrombin generation and risk for venous thrombosis among homozygous FVL and heterozygous for FVL with partial FV deficiency (pseudo-homozygous APC resistance) when compared to subjects genotyped as heterozygous for the FVL mutation (wild-type FV activity preserved) [40]. Here we found that littermate hemophilic mice heterozygous and homozygous for FVL presented improvement of both in vitro and in vivo hemostatic parameters at similar fashion. These data suggest that it is slow inactivation of FVa with consequently procoagulant activity that underlying the potential benefits of FVL in hemophilia. Therefore, it is possible that murine FV does not present cofactor activity on FVIIIa-inactivation by APC. Although these experimental conditions may present distinct underlying mechanisms, data obtained in both genetic models and protein injection demonstrate the beneficial effects of the enhancement in thrombin levels, as the final outcome, and suggest that other alternative therapeutic approaches for hemophilia could be investigated.

In summary, this work demonstrated that the FVL mutation enhances hemostasis in hemophilia A or B mice as judged by the improvement of the clotting times and by the in vivo ability to form clots. Because FVL has markedly beneficial effects at the microcirculation level in an injury that predominantly does not expose the subendothelium, the protection against hemorrhagic challenges are likely to impact minor bleedings, but not those trauma-induced hemorrhages. These data explain in part the heterogeneity of the clinical diversity observed for the severe hemophilia phenotype with FVL especially among adults.

REFERENCES

1. Roberts H R, Hoffman M. Hemophilia A and hemophilia B. In. Beutler E, Coller B, Lichtman M, Kipps T, Seligsohn U, editors. Hematology. 6th ed. New York: McGraw Hill; 2001. p. 1639-1657.
2. Tuddenham E G, Schwaab R, Seehafer J, Millar D S, Gitschier J, Higuchi M, Bidichandani S, Connor J M, Hoyer L W, Yoshioka A, et al. Haemophilia A: database of nucleotide substitutions, deletions, insertions and rearrangements of the factor VIII gene, second edition. Nucleic Acids Res 1994; 22:3511-33.
3. Aledort L M, Haschmeyer R H, Pettersson H. A longitudinal study of orthopaedic outcomes for severe factor-VIII-deficient haemophiliacs. The Orthopaedic Outcome Study Group. J Intern Med 1994; 236:391-9.
4. Molho P, Rolland N, Lebrun T, Dirat G, Courpied J P, Croughs T, Duprat I, Sultan Y. Epidemiological survey of the orthopaedic status of severe haemophilia A and B patients in France. The French Study Group. secretariat.haemophiles@cch.ap-hop-paris.fr. Haemophilia 2000; 6:23-32.
5. Esmon C T. The protein C pathway. Chest 2003; 124:26 S-32S.
6. Mann K G, Kalafatis M. Factor V: a combination of Dr Jekyll and Mr Hyde. Blood 2003; 101:20-30.
7. Dahlback B, Carlsson M, Svensson P J. Familial thrombophilia due to a previously unrecognized mechanism characterized by poor anticoagulant response to activated protein C: prediction of a cofactor to activated protein C. Proc Natl Acad Sci USA 1993; 90:1004-8.
8. Bertina R, Koeleman B, Kostner B, Rosendaal F, Dirven R, Ronde H, Velden P, Reitsma P. Mutation in blood coagulation factor V associated with resistance to activated protein C. Nature 1994; 369:64-67.
9. Nichols W C, Amano K, Cacheris P M, Figueiredo M S, Michaelides K, Schwaab R, Hoyer L, Kaufman R J, Ginsburg D. Moderation of hemophilia A phenotype by the factor V R506Q mutation. Blood 1996; 88:1183-7.
10. Lee D H, Walker I R, Teitel J, Poon M C, Ritchie B, Akabutu J, Sinclair G D, Pai M, Wu J W, Reddy S, Carter C, Growe G, Lillicrap D, Lam M, Blajchman M A. Effect of the factor V Leiden mutation on the clinical expression of severe hemophilia A. Thromb Haemost 2000; 83:387-91.
11. Arbini A A, Mannucci P M, Bauer K A. Low prevalence of the factor V Leiden mutation among "severe" hemophiliacs with a "milder" bleeding diathesis. Thromb Haemost 1995; 74:1255-8.
12. Arruda V, Annichino-Bizzacchi J, Antunes S, Costa F. Association of severe hemophilia A and factor V Leiden: report of three cases. Haemophilia 1996; 2:51-53.
13. Chang J, Weinman A F, Thompson A R. Factor V Arg/Gln306 has no dominant influence of the severity of hemophilia when inherited concurrently. Throm Haemost 1995; 73:1368.
14. Escuriola Ettingshausen C, Halimeh S, Kumik K, Schobess R, Wermes C, Junker R, Kreuz W, Pollmann H, Nowak-Gottl U. Symptomatic onset of severe hemophilia A in childhood is dependent on the presence of prothrombotic risk factors. Thromb Haemost 2001; 85:218-20.
15. van't Veer C, Golden N J, Kalafatis M, Simioni P, Bertina R M, Mann K G. An in vitro analysis of the combination of hemophilia A and factor V(LEIDEN). Blood 1997; 90:3067-72.
16. Bos M, Meijerman D, Van der Zwaan C, Mertens K. Does activated protein C-resistant factor V contribute to thrombin generation in hemophilic plasma? J Thromb Haemost 2005; 3:1-9.
17. Broze G J, Jr., Higuchi D A. Coagulation-dependent inhibition of fibrinolysis: role of carboxypeptidase-U and the premature lysis of clots from hemophilic plasma. Blood 1996; 88:3815-23.
18. Bajzar L, Kalafatis M, Simioni P, Tracy P B. An antifibrinolytic mechanism describing the prothrombotic effect associated with factor VLeiden. J Biol Chem 1996; 271: 22949-52.
19. Parker A C, Mundada L V, Schmaier A H, Fay W P. Factor VLeiden inhibits fibrinolysis in vivo. Circulation 2004; 110:3594-8.
20. Bi L, Lawler A M, Antonarakis S E, High K A, Gearhart J D, Kazazian H H. Targeted disruption of the mouse factor VIII gene produces a model of haemophilia. Nat Genet. 1995; 10:119-121.
21. Kung J, Hagstrom J, Cass D, Tai S, Lin H F, Stafford D W, High K A. Human F.IX corrects the bleeding diathesis of mice with hemophilia B. Blood 1998; 91:784-790.
22. Cui J, Eitzman D, Westrick R, Christie P, Xu Z, Yang A, Prurkayastha A, Yang T, Metz A, Gallagher K, Tyson J, Rosenberg R, Ginsburg D. Spontaneous thrombosis in mice carrying the factor V Leiden mutation. Blood 2000; 96:4222-4226.
23. Fields P A, Kowalczyk D W, Arruda V R, Armstrong E, McCleland M L, Hagstrom J N, Pasi K J, Ertl H C, Herzog R W, High K A. Role of vector in activation of T cell subsets in immune responses against the secreted transgene product factor IX. Mol Ther 2000; 1:225-35.
24. Lin H F, Maeda N, Smithies O, Straight D L, Stafford D W. A coagulation factor IX-deficient mouse model for human hemophilia B. Blood 1997; 90:3962-6.
25. Ravanat C, Freund M, Dol F, Cadroy Y, Roussi J, Incardona F, Maffrand J, Boneu B, Drouet L, Legrand C, Herbet J, Cazenave J. Cross-reactivity of human molecular markers for detection of prethrombotic states in various animal species. Blood Coag Fibrinol 1995; 6:446-455.
26. Schuettrumpf J, Herzog R W, Schlachterman A, Kaufhold A, Stafford D W, Arruda V R. Factor IX variants improve gene therapy efficacy for hemophilia B. Blood 2004; 105: 2316-23.
27. Farrehi P M, Ozaki C K, Carmeliet P, Fay W P. Regulation of arterial thrombolysis by plasminogen activator inhibitor-1 in mice. Circulation 1998; 97: 1002-8.
28. Falati S, Gross P, Merrill-Skoloff G, Furie B C, Furie B. Real-time in vivo imaging of platelets, tissue factor and fibrin during arterial thrombus formation in the mouse. Nat Med 2002; 8:1175-81.
29. Toso R, Camire R M. Removal of B-domain sequences from factor V rather than specific proteolysis underlies the mechanism by which cofactor function is realized. J Biol Chem 2004; 279:21643-50.
30. Ni H, Denis C V, Subbarao S, Degen J L, Sato T N, Hynes R O, Wagner D D. Persistence of platelet thrombus formation in arterioles of mice lacking both von Willebrand factor and fibrinogen. J Clin Invest 2000; 106:385-92.
31. Rosen E D, Raymond S, Zollman A, Noria F, Sandoval-Cooper M, Shulman A, Merz I L, Castellino F J. Laser-induced noninvasive vascular injury models in mice generate platelet- and coagulation-dependent thrombi. Am J Pathol 2001; 158: 1613-22.
32. Camire R M, Pollak E S, Kaushansky K, Tracy P B. Secretable human platelet-derived factor V originates from the plasma pool. Blood 1998; 92:3035-41.

33. Sun H, Yang T L, Yang A, Wang X, Ginsburg D. The murine platelet and plasma factor V pools are biosynthetically distinct and sufficient for minimal hemostasis. Blood 2003; 102.2856-61.
34. Fernandez J A, Xu X, Liu D, Zlokovic B V, Griffin J H. Recombinant murine-activated protein C is neuroprotective in a murine ischemic stroke model. Blood Cells Mol Dis 2003; 30:271-6.
35. Uhrin P, Dewerchin M, Hilpert M, Chrenek P, Schofer C, Zechmeister-Machhart M, Kronke G, Vales A, Carmeliet P, Binder B R, Geiger M. Disruption of the protein C inhibitor gene results in impaired spermatogenesis and male infertility. J Clin Invest 2000; 106:1531-9.
36. Esmon C T, Ding W, Yasuhiro K, Gu J M, Ferrell G, Regan L M, Stearns-Kurosawa D J, Kurosawa S, Mather T, Laszik Z, Esmon N L. The protein C pathway: new insights. Thromb Haemost 1997; 78:70-4.
37. Esmon C T. The roles of protein C and thrombomodulin in the regulation of blood coagulation. J Biol Chem 1989; 264:4743-6.
38. Laszik Z, Mitro A, Taylor F B, Jr., Ferrell G, Esmon C T. Human protein C receptor is present primarily on endothelium of large blood vessels: implications for the control of the protein C pathway. Circulation 1997; 96:3633-40.
39. Cawthern K M, van't Veer C, Lock J B, DiLorenzo M E, Branda R F, Mann K G. Blood coagulation in hemophilia A and hemophilia C. Blood 1998; 91:4581-92.
40. Simioni P, Castoldi E, Lunghi B, Tormene D, Rosing J, Bernardi F. An underestimated combination of opposites resulting in enhanced thrombotic tendency. Blood 2005.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for the treatment of a hemophilia A or hemophilia B in a patient in need thereof, comprising administering an effective amount of an activated form of factor V (FV), said activated form of FV selected from the group consisting of FV-810 (FV, SEQ ID NO: 1 lacking amino acid residues 811-1491); FV-859 (FV, SEQ ID NO: 1 lacking amino acid residues 860-1491); FV-866 (FV, SEQ ID NO: 1 lacking amino acid residues 867-1491); FV-902 (FV, SEQ ID NO: 1 lacking amino acid residues 903-1491); FV-924 (FV, SEQ ID NO: 1 lacking amino acid residues 923-1491); FV-937 (FV, SEQ ID NO: 1 lacking amino acid residues 938-1491); FV-956 (FV, SEQ ID NO: 1 lacking amino acid residues 957-1491); FV-1033-B58-s131 (FV, SEQ ID NO: 1 lacking amino acid residues 1034-1491 with amino acid residues 900-1030 exchanged with amino acid residues 907-1037 of factor VIII of SEQ ID NO: 2; FV-1033-B58-s104 (FV, SEQ ID NO: 1 lacking amino acid residues 1034-1491 with amino acid residues 904-1007 exchanged with amino acid residues 972-1075 of factor VIII of SEQ ID NO: 2); and FV-1033-B58-s46 (FV, SEQ ID NO: 1 lacking amino acid residues 1034-1491 with amino acid residues 963-1008 exchanged with amino acid residues 1032-1077 of factor VIII of SEQ ID NO: 2), thereby enhancing clot formation in said patient and ameliorating the symptoms of said hemophilia.

2. The method of claim 1, wherein the disorder is hemophilia A.

3. The method of claim 1, wherein the disorder is hemophilia B.

4. The method of claim 1, wherein said activated form of FV is delivered intravenously.

5. The method of claim 1, wherein said activated form of FV is administered intravenously at least once a day at a dosage between about 10 and 500 µg/kg.

6. A method for enhancing clot formation in a patient in need thereof, said patient having hemophilia or needing treatment due to administration of an agent selected from the group consisting of heparin, low molecular weight heparin, pentasaccharide, warfarin, small molecule antithrombotics and FXa inhibitors, said method comprising administering an effective amount of an activated form of FV of SEQ ID NO: 1, wherein at least one of the arginine residues at positions 506, 306, and 679 of said activated form of FV of SEQ ID NO: 1 is replaced with an amino acid other than arginine, and wherein said activated form of FV is selected from the group consisting of FV-810 (FV, SEQ ID NO: 1 lacking amino acid residues 811-1491); FV-859 (FV, SEQ ID NO: 1 lacking amino acid residues 860-1491); FV-866 (FV, SEQ ID NO: 1 lacking amino acid residues 867-1491); FV-902 (FV, SEQ ID NO: 1 lacking amino acid residues 903-1491); FV-924 (FV, SEQ ID NO: 1 lacking amino acid residues 923-1491); FV-937 (FV, SEQ ID NO: 1 lacking amino acid residues 938-1491); FV-956 (FV, SEQ ID NO: 1 lacking amino acid residues 957-1491); FV-1033-B58-s131 (FV, SEQ ID NO: 1 lacking amino acid residues 1034-1491 with amino acid residues 900-1030 exchanged with amino acid residues 907-1037 of factor VIII of SEQ ID NO: 2; FV-1033-B58-s104 (FV, SEQ ID NO: 1 lacking amino acid residues 1034-1491 with amino acid residues 904-1007 exchanged with amino acid residues 972-1075 of factor VIII of SEQ ID NO: 2); and FV-1033-B58-s46 (FV, SEQ ID NO: 1 lacking amino acid residues 1034-1491 with amino acid residues 963-1008 exchanged with amino acid residues 1032-1077 of factor VIII of SEQ ID NO: 2), thereby enhancing clot formation in said hemophilia patient or said patient needing treatment due to administration of an agent selected from the group consisting of heparin, low molecular weight heparin, pentasaccharide, warfarin, small molecule antithrombotics and FXa inhibitors.

7. A method for enhancing clot formation in a patient in need thereof, said patient needing treatment due to administration of an agent selected from the group consisting of heparin, low molecular weight heparin, pentasaccharide, warfarin, small molecule antithrombotics and FXa inhibitors, said method comprising administering an effective amount of an activated form of factor V (FV), said activated form of FV selected from the group consisting of FV-859 (FV of SEQ ID NO: 1 lacking amino acid residues 860-1491; FV-924 (FV of SEQ ID NO: 1 lacking amino acid residues 923-1491); FV-937 (FV of SEQ ID NO: 1 lacking amino acid residues 938-1491); FV-1033-B58-s131 (FV of SEQ ID NO: 1 lacking amino acid residues 1034-1491 with amino acid residues 900-1030 exchanged with amino acid residues 907-1037 of factor VIII of SEQ ID NO: 2); FV-1033-B58-s104 (FV of SEQ ID NO: 1 lacking amino acid residues 1034-1491 with amino acid residues 904-1007 exchanged with amino acid residues 972-1075 of factor VIII of SEQ ID NO: 2); and FV-1033-B58-s46 (FV of SEQ ID NO: 1 lacking amino acid residues 1034-1491 with amino acid residues 963-1008 exchanged with amino acid residues 1032-1077 of factor VIII of SEQ ID NO: 2), thereby enhancing clot formation in said patient needing treatment due to administration of an agent selected from the group consisting of heparin, low molecular weight heparin, pentasaccharide, warfarin, small molecule antithrombotics and FXa inhibitors.

* * * * *

SEQUENCE LISTING

```
<160> NUMBER OF SEQ ID NOS: 2

<210> SEQ ID NO 1
<211> LENGTH: 2196
<212> TYPE: PRT
<213> ORGANISM: Homo Sapiens

<400> SEQUENCE: 1

Ala Gln Leu Arg Gln Phe Tyr Val Ala Ala Gln Gly Ile Ser Trp Ser
1               5                   10                  15

Tyr Arg Pro Glu Pro Thr Asn Ser Ser Leu Asn Leu Ser Val Thr Ser
                20                  25                  30

Phe Lys Lys Ile Val Tyr Arg Glu Tyr Glu Pro Tyr Phe Lys Lys Glu
            35                  40                  45

Lys Pro Gln Ser Thr Ile Ser Gly Leu Leu Gly Pro Thr Leu Tyr Ala
        50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Tyr Leu Asp His Thr Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240
```

```
Ile His Phe Asn Gly Gln Val Leu Glu Gln Asn His His Lys Val Ser
            245                 250                 255

Ala Ile Thr Leu Val Ser Ala Thr Ser Thr Thr Ala Asn Met Thr Val
            260                 265                 270

Gly Pro Glu Gly Lys Trp Ile Ile Ser Ser Leu Thr Pro Lys His Leu
            275                 280                 285

Gln Ala Gly Met Gln Ala Tyr Ile Asp Ile Lys Asn Cys Pro Lys Lys
            290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
                340                 345                 350

Asp Asn Phe Ser Asn Gln Ile Gly Lys His Tyr Lys Lys Val Met Tyr
                355                 360                 365

Thr Gln Tyr Glu Asp Glu Ser Phe Thr Lys His Thr Val Asn Pro Asn
            370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
                420                 425                 430

Ser Ser Phe Thr Ser Gly Arg Asn Asn Thr Met Ile Arg Ala Val Gln
            435                 440                 445

Pro Gly Glu Thr Tyr Thr Tyr Lys Trp Asn Ile Leu Glu Phe Asp Glu
            450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
                500                 505                 510

Asp Ile Glu Gln Gln Ala Val Phe Ala Val Phe Asp Glu Asn Lys Ser
            515                 520                 525

Trp Tyr Leu Glu Asp Asn Ile Asn Lys Phe Cys Glu Asn Pro Asp Glu
            530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
            595                 600                 605

His Glu Asp Thr Leu Thr Leu Phe Pro Met Arg Gly Glu Ser Val Thr
            610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
```

-continued

```
                660                 665                 670
Ser Thr Val Met Ala Thr Arg Lys Met His Asp Arg Leu Glu Pro Glu
            675                 680                 685
Asp Glu Glu Ser Asp Ala Asp Tyr Asp Tyr Gln Asn Arg Leu Ala Ala
            690                 695                 700
Ala Leu Gly Ile Arg Ser Phe Arg Asn Ser Ser Leu Asn Gln Glu Glu
705                 710                 715                 720
Glu Glu Phe Asn Leu Thr Ala Leu Ala Leu Gly Asn Gly Thr Glu Phe
                725                 730                 735
Val Ser Ser Asn Thr Asp Ile Ile Val Gly Ser Asn Tyr Ser Ser Pro
            740                 745                 750
Ser Asn Ile Ser Lys Phe Thr Val Asn Asn Leu Ala Glu Pro Gln Lys
            755                 760                 765
Ala Pro Ser His Gln Gln Ala Thr Ala Gly Ser Pro Leu Arg His
            770                 775                 780
Leu Ile Gly Lys Asn Ser Val Leu Asn Ser Ser Thr Ala Glu His Ser
785                 790                 795                 800
Ser Pro Tyr Ser Glu Asp Pro Ile Glu Asp Pro Leu Gln Pro Asp Val
                805                 810                 815
Thr Gly Ile Arg Leu Leu Ser Leu Gly Ala Gly Glu Phe Arg Ser Gln
                820                 825                 830
Glu His Ala Lys Arg Lys Gly Pro Lys Val Glu Arg Asp Gln Ala Ala
            835                 840                 845
Lys His Arg Phe Ser Trp Met Lys Leu Leu Ala His Lys Val Gly Arg
            850                 855                 860
His Leu Ser Gln Asp Thr Gly Ser Pro Ser Gly Met Arg Pro Trp Glu
865                 870                 875                 880
Asp Leu Pro Ser Gln Asp Thr Gly Ser Pro Ser Arg Met Arg Pro Trp
                885                 890                 895
Glu Asp Pro Pro Ser Asp Leu Leu Leu Lys Gln Ser Asn Ser Ser
            900                 905                 910
Lys Ile Leu Val Gly Arg Trp His Leu Ala Ser Glu Lys Gly Ser Tyr
            915                 920                 925
Glu Ile Ile Gln Asp Thr Asp Glu Asp Thr Ala Val Asn Asn Trp Leu
            930                 935                 940
Ile Ser Pro Gln Asn Ala Ser Arg Ala Trp Gly Glu Ser Thr Pro Leu
945                 950                 955                 960
Ala Asn Lys Pro Gly Lys Gln Ser Gly His Pro Lys Phe Pro Arg Val
                965                 970                 975
Arg His Lys Ser Leu Gln Val Arg Gln Asp Gly Gly Lys Ser Arg Leu
            980                 985                 990
Lys Lys Ser Gln Phe Leu Ile Lys Thr Arg Lys Lys Lys Glu Lys
            995                 1000                1005
His Thr His His Ala Pro Leu Ser Pro Arg Thr Phe His Pro Leu Arg
            1010                1015                1020
Ser Glu Ala Tyr Asn Thr Phe Ser Glu Arg Arg Leu Lys His Ser Leu
1025                1030                1035                1040
Val Leu His Lys Ser Asn Glu Thr Ser Leu Pro Thr Asp Leu Asn Gln
                1045                1050                1055
Thr Leu Pro Ser Met Asp Phe Gly Trp Ile Ala Ser Leu Pro Asp His
                1060                1065                1070
Asn Gln Asn Ser Ser Asn Asp Thr Gly Gln Ala Ser Cys Pro Pro Gly
            1075                1080                1085
```

```
Leu Tyr Gln Thr Val Pro Pro Glu His Tyr Gln Thr Phe Pro Ile
    1090                1095                1100

Gln Asp Pro Asp Gln Met His Ser Thr Ser Asp Pro Ser His Arg Ser
1105                1110                1115                1120

Ser Ser Pro Glu Leu Ser Glu Met Leu Glu Tyr Asp Arg Ser His Lys
                1125                1130                1135

Ser Phe Pro Thr Asp Ile Ser Gln Met Ser Pro Ser Ser Glu His Glu
                1140                1145                1150

Val Trp Gln Thr Val Ile Ser Pro Asp Leu Ser Gln Val Thr Leu Ser
                1155                1160                1165

Pro Glu Leu Ser Gln Thr Asn Leu Ser Pro Asp Leu Ser His Thr Thr
                1170                1175                1180

Leu Ser Pro Glu Leu Ile Gln Arg Asn Leu Ser Pro Ala Leu Gly Gln
1185                1190                1195                1200

Met Pro Ile Ser Pro Asp Leu Ser His Thr Thr Leu Ser Pro Asp Leu
                1205                1210                1215

Ser His Thr Thr Leu Ser Leu Asp Leu Ser Gln Thr Asn Leu Ser Pro
                1220                1225                1230

Glu Leu Ser Gln Thr Asn Leu Ser Pro Ala Leu Gly Gln Met Pro Leu
                1235                1240                1245

Ser Pro Asp Leu Ser His Thr Thr Leu Ser Leu Asp Phe Ser Gln Thr
                1250                1255                1260

Asn Leu Ser Pro Glu Leu Ser His Met Thr Leu Ser Pro Glu Leu Ser
1265                1270                1275                1280

Gln Thr Asn Leu Ser Pro Ala Leu Gly Gln Met Pro Ile Ser Pro Asp
                1285                1290                1295

Leu Ser His Thr Thr Leu Ser Leu Asp Phe Ser Gln Thr Asn Leu Ser
                1300                1305                1310

Pro Glu Leu Ser Gln Thr Asn Leu Ser Pro Ala Leu Gly Gln Met Pro
                1315                1320                1325

Leu Ser Pro Asp Pro Ser His Thr Thr Leu Ser Leu Asp Leu Ser Gln
                1330                1335                1340

Thr Asn Leu Ser Pro Glu Leu Ser Gln Thr Asn Leu Ser Pro Asp Leu
1345                1350                1355                1360

Ser Glu Met Pro Leu Phe Ala Asp Leu Ser Gln Ile Pro Leu Thr Pro
                1365                1370                1375

Asp Leu Asp Gln Met Thr Leu Ser Pro Asp Leu Gly Glu Thr Asp Leu
                1380                1385                1390

Ser Pro Asn Phe Gly Gln Met Ser Leu Ser Pro Asp Leu Ser Gln Val
                1395                1400                1405

Thr Leu Ser Pro Asp Ile Ser Asp Thr Thr Leu Leu Pro Asp Leu Ser
                1410                1415                1420

Gln Ile Ser Pro Pro Asp Leu Asp Gln Ile Phe Tyr Pro Ser Glu
1425                1430                1435                1440

Ser Ser Gln Ser Leu Leu Leu Gln Glu Phe Asn Glu Ser Phe Pro Tyr
                1445                1450                1455

Pro Asp Leu Gly Gln Met Pro Ser Pro Ser Ser Pro Thr Leu Asn Asp
                1460                1465                1470

Thr Phe Leu Ser Lys Glu Phe Asn Pro Leu Val Ile Val Gly Leu Ser
                1475                1480                1485

Lys Asp Gly Thr Asp Tyr Ile Glu Ile Ile Pro Lys Glu Glu Val Gln
                1490                1495                1500

Ser Ser Glu Asp Asp Tyr Ala Glu Ile Asp Tyr Val Pro Tyr Asp Asp
1505                1510                1515                1520
```

```
Pro Tyr Lys Thr Asp Val Arg Thr Asn Ile Asn Ser Ser Arg Asp Pro
            1525                1530                1535

Asp Asn Ile Ala Ala Trp Tyr Leu Arg Ser Asn Asn Gly Asn Arg Arg
            1540                1545                1550

Asn Tyr Tyr Ile Ala Ala Glu Glu Ile Ser Trp Asp Tyr Ser Glu Phe
        1555                1560                1565

Val Gln Arg Glu Thr Asp Ile Glu Asp Ser Asp Ile Pro Glu Asp
        1570                1575                1580

Thr Thr Tyr Lys Lys Val Val Phe Arg Lys Tyr Leu Asp Ser Thr Phe
1585                1590                1595                1600

Thr Lys Arg Asp Pro Arg Gly Glu Tyr Glu Glu His Leu Gly Ile Leu
            1605                1610                1615

Gly Pro Ile Ile Arg Ala Glu Val Asp Asp Val Ile Gln Val Arg Phe
            1620                1625                1630

Lys Asn Leu Ala Ser Arg Pro Tyr Ser Leu His Ala His Gly Leu Ser
            1635                1640                1645

Tyr Glu Lys Ser Ser Glu Gly Lys Thr Tyr Glu Asp Asp Ser Pro Glu
            1650                1655                1660

Trp Phe Lys Glu Asp Asn Ala Val Gln Pro Asn Ser Ser Tyr Thr Tyr
1665                1670                1675                1680

Val Trp His Ala Thr Glu Arg Ser Gly Pro Glu Ser Pro Gly Ser Ala
            1685                1690                1695

Cys Arg Ala Trp Ala Tyr Tyr Ser Ala Val Asn Pro Glu Lys Asp Ile
            1700                1705                1710

His Ser Gly Leu Ile Gly Pro Leu Leu Ile Cys Gln Lys Gly Ile Leu
            1715                1720                1725

His Lys Asp Ser Asn Met Pro Val Asp Met Arg Glu Phe Val Leu Leu
            1730                1735                1740

Phe Met Thr Phe Asp Glu Lys Lys Ser Trp Tyr Tyr Glu Lys Lys Ser
1745                1750                1755                1760

Arg Ser Ser Trp Arg Leu Thr Ser Ser Glu Met Lys Lys Ser His Glu
            1765                1770                1775

Phe His Ala Ile Asn Gly Met Ile Tyr Ser Leu Pro Gly Leu Lys Met
            1780                1785                1790

Tyr Glu Gln Glu Trp Val Arg Leu His Leu Leu Asn Ile Gly Gly Ser
            1795                1800                1805

Gln Asp Ile His Val Val His Phe His Gly Gln Thr Leu Leu Glu Asn
            1810                1815                1820

Gly Asn Lys Gln His Gln Leu Gly Val Trp Pro Leu Leu Pro Gly Ser
1825                1830                1835                1840

Phe Lys Thr Leu Glu Met Lys Ala Ser Lys Pro Gly Trp Trp Leu Leu
            1845                1850                1855

Asn Thr Glu Val Gly Glu Asn Gln Arg Ala Gly Met Gln Thr Pro Phe
            1860                1865                1870

Leu Ile Met Asp Arg Asp Cys Arg Met Pro Met Gly Leu Ser Thr Gly
            1875                1880                1885

Ile Ile Ser Asp Ser Gln Ile Lys Ala Ser Glu Phe Leu Gly Tyr Trp
            1890                1895                1900

Glu Pro Arg Leu Ala Arg Leu Asn Asn Gly Gly Ser Tyr Asn Ala Trp
1905                1910                1915                1920

Ser Val Glu Lys Leu Ala Ala Glu Phe Ala Ser Lys Pro Trp Ile Gln
            1925                1930                1935

Val Asp Met Gln Lys Glu Val Ile Ile Thr Gly Ile Gln Thr Gln Gly
```

-continued

```
                  1940            1945            1950
Ala Lys His Tyr Leu Lys Ser Cys Tyr Thr Thr Glu Phe Tyr Val Ala
        1955            1960            1965

Tyr Ser Ser Asn Gln Ile Asn Trp Gln Ile Phe Lys Gly Asn Ser Thr
    1970            1975            1980

Arg Asn Val Met Tyr Phe Asn Gly Asn Ser Asp Ala Ser Thr Ile Lys
1985            1990            1995            2000

Glu Asn Gln Phe Asp Pro Pro Ile Val Ala Arg Tyr Ile Arg Ile Ser
        2005            2010            2015

Pro Thr Arg Ala Tyr Asn Arg Pro Thr Leu Arg Leu Glu Leu Gln Gly
        2020            2025            2030

Cys Glu Val Asn Gly Cys Ser Thr Pro Leu Gly Met Glu Asn Gly Lys
        2035            2040            2045

Ile Glu Asn Lys Gln Ile Thr Ala Ser Ser Phe Lys Lys Ser Trp Trp
        2050            2055            2060

Gly Asp Tyr Trp Glu Pro Phe Arg Ala Arg Leu Asn Ala Gln Gly Arg
2065            2070            2075            2080

Val Asn Ala Trp Gln Ala Lys Ala Asn Asn Lys Gln Trp Leu Glu
        2085            2090            2095

Ile Asp Leu Leu Lys Ile Lys Lys Ile Thr Ala Ile Ile Thr Gln Gly
        2100            2105            2110

Cys Lys Ser Leu Ser Ser Glu Met Tyr Val Lys Ser Tyr Thr Ile His
        2115            2120            2125

Tyr Ser Glu Gln Gly Val Glu Trp Lys Pro Tyr Arg Leu Lys Ser Ser
        2130            2135            2140

Met Val Asp Lys Ile Phe Glu Gly Asn Thr Asn Thr Lys Gly His Val
2145            2150            2155            2160

Lys Asn Phe Phe Asn Pro Pro Ile Ile Ser Arg Phe Ile Arg Val Ile
        2165            2170            2175

Pro Lys Thr Trp Asn Gln Ser Ile Thr Leu Arg Leu Glu Leu Phe Gly
        2180            2185            2190

Cys Asp Ile Tyr
        2195

<210> SEQ ID NO 2
<211> LENGTH: 2332
<212> TYPE: PRT
<213> ORGANISM: Homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
            85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
```

```
            115                 120                 125
Phe Pro Gly Gly Ser His Thr Tyr Val Trp Gln Val Leu Lys Glu Asn
130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Lys Thr Gln Thr Leu
                180                 185                 190
His Lys Phe Ile Leu Leu Phe Ala Val Phe Asp Glu Gly Lys Ser Trp
                195                 200                 205
His Ser Glu Thr Lys Asn Ser Leu Met Gln Asp Arg Asp Ala Ala Ser
        210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Leu Thr Asp
                340                 345                 350
Ser Glu Met Asp Val Val Arg Phe Asp Asp Asn Ser Pro Ser Phe
            355                 360                 365
Ile Gln Ile Arg Ser Val Ala Lys Lys His Pro Lys Thr Trp Val His
    370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
    530                 535                 540
```

-continued

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
              980                 985                 990

Val Ser Ile Ser Leu Leu Lys Thr Asn Lys Thr Ser Asn Asn Ser Ala
              995                1000                1005

Thr Asn Arg Lys Thr His Ile Asp Gly Pro Ser Leu Leu Ile Glu Asn
           1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
                1045                1050                1055

Thr Ala Leu Arg Leu Asn His Met Ser Asn Lys Thr Thr Ser Ser Lys
              1060                1065                1070

Asn Met Glu Met Val Gln Gln Lys Lys Glu Gly Pro Ile Pro Pro Asp
              1075                1080                1085

Ala Gln Asn Pro Asp Met Ser Phe Phe Lys Met Leu Phe Leu Pro Glu
1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
              1125                1130                1135

Ser Val Glu Gly Gln Asn Phe Leu Ser Glu Lys Asn Lys Val Val Val
              1140                1145                1150

Gly Lys Gly Glu Phe Thr Lys Asp Val Gly Leu Lys Glu Met Val Phe
              1155                1160                1165

Pro Ser Ser Arg Asn Leu Phe Leu Thr Asn Leu Asp Asn Leu His Glu
              1170                1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
              1205                1210                1215

Val Thr Gly Thr Lys Asn Phe Met Lys Asn Leu Phe Leu Leu Ser Thr
              1220                1225                1230

Arg Gln Asn Val Glu Gly Ser Tyr Glu Gly Ala Tyr Ala Pro Val Leu
              1235                1240                1245

Gln Asp Phe Arg Ser Leu Asn Asp Ser Thr Asn Arg Thr Lys Lys His
              1250                1255                1260

Thr Ala His Phe Ser Lys Lys Gly Glu Glu Glu Asn Leu Glu Gly Leu
1265                1270                1275                1280

Gly Asn Gln Thr Lys Gln Ile Val Glu Lys Tyr Ala Cys Thr Thr Arg
              1285                1290                1295

Ile Ser Pro Asn Thr Ser Gln Gln Asn Phe Val Thr Gln Arg Ser Lys
              1300                1305                1310

Arg Ala Leu Lys Gln Phe Arg Leu Pro Leu Glu Glu Thr Glu Leu Glu
              1315                1320                1325

Lys Arg Ile Ile Val Asp Asp Thr Ser Thr Gln Trp Ser Lys Asn Met
              1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
              1365                1370                1375

Ser His Ser Ile Pro Gln Ala Asn Arg Ser Pro Leu Pro Ile Ala Lys
              1380                1385                1390

Val Ser Ser Phe Pro Ser Ile Arg Pro Ile Tyr Leu Thr Arg Val Leu

```
                1395                1400                1405
Phe Gln Asp Asn Ser Ser His Leu Pro Ala Ala Ser Tyr Arg Lys Lys
    1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
            1445                1450                1455

Arg Glu Val Gly Ser Leu Gly Thr Ser Ala Thr Asn Ser Val Thr Tyr
        1460                1465                1470

Lys Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys Asp
    1490                1495                1500

Leu Phe Pro Thr Glu Thr Ser Asn Gly Ser Pro Gly His Leu Asp Leu
1505                1510                1515                1520

Val Glu Gly Ser Leu Leu Gln Gly Thr Glu Gly Ala Ile Lys Trp Asn
            1525                1530                1535

Glu Ala Asn Arg Pro Gly Lys Val Pro Phe Leu Arg Val Ala Thr Glu
        1540                1545                1550

Ser Ser Ala Lys Thr Pro Ser Lys Leu Leu Asp Pro Leu Ala Trp Asp
    1555                1560                1565

Asn His Tyr Gly Thr Gln Ile Pro Lys Glu Glu Trp Lys Ser Gln Glu
    1570                1575                1580

Lys Ser Pro Glu Lys Thr Ala Phe Lys Lys Lys Asp Thr Ile Leu Ser
1585                1590                1595                1600

Leu Asn Ala Cys Glu Ser Asn His Ala Ile Ala Ala Ile Asn Glu Gly
            1605                1610                1615

Gln Asn Lys Pro Glu Ile Glu Val Thr Trp Ala Lys Gln Gly Arg Thr
        1620                1625                1630

Glu Arg Leu Cys Ser Gln Asn Pro Pro Val Leu Lys Arg His Gln Arg
    1635                1640                1645

Glu Ile Thr Arg Thr Thr Leu Gln Ser Asp Gln Glu Glu Ile Asp Tyr
    1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
            1685                1690                1695

His Tyr Phe Ile Ala Ala Val Glu Arg Leu Trp Asp Tyr Gly Met Ser
        1700                1705                1710

Ser Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe Thr
    1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
            1765                1770                1775

Asn Gln Ala Ser Arg Pro Tyr Ser Phe Tyr Ser Ser Leu Ile Ser Tyr
        1780                1785                1790

Glu Glu Asp Gln Arg Gln Gly Ala Glu Pro Arg Lys Asn Phe Val Lys
    1795                1800                1805

Pro Asn Glu Thr Lys Thr Tyr Phe Trp Lys Val Gln His His Met Ala
    1810                1815                1820
```

-continued

```
Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
            1845                1850                1855

Val Cys His Thr Asn Thr Leu Asn Pro Ala His Gly Arg Gln Val Thr
        1860                1865                1870

Val Gln Glu Phe Ala Leu Phe Phe Thr Ile Phe Asp Glu Thr Lys Ser
    1875                1880                1885

Trp Tyr Phe Thr Glu Asn Met Glu Arg Asn Cys Arg Ala Pro Cys Asn
1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
            1925                1930                1935

Asp Gln Arg Ile Arg Trp Tyr Leu Leu Ser Met Gly Ser Asn Glu Asn
        1940                1945                1950

Ile His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe Glu
1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
            2005                2010                2015

Tyr Ser Asn Lys Cys Gln Thr Pro Leu Gly Met Ala Ser Gly His Ile
        2020                2025                2030

Arg Asp Phe Gln Ile Thr Ala Ser Gly Gln Tyr Gly Gln Trp Ala Pro
    2035                2040                2045

Lys Leu Ala Arg Leu His Tyr Ser Gly Ser Ile Asn Ala Trp Ser Thr
2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
            2085                2090                2095

Tyr Ile Ser Gln Phe Ile Ile Met Tyr Ser Leu Asp Gly Lys Lys Trp
        2100                2105                2110

Gln Thr Tyr Arg Gly Asn Ser Thr Gly Thr Leu Met Val Phe Phe Gly
    2115                2120                2125

Asn Val Asp Ser Ser Gly Ile Lys His Asn Ile Phe Asn Pro Pro Ile
2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
            2165                2170                2175

Pro Leu Gly Met Glu Ser Lys Ala Ile Ser Asp Ala Gln Ile Thr Ala
        2180                2185                2190

Ser Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val Asn
2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
            2245                2250                2255
```

-continued

```
Val Lys Glu Phe Leu Ile Ser Ser Ser Gln Asp Gly His Gln Trp Thr
            2260                2265                2270

Leu Phe Phe Gln Asn Gly Lys Val Lys Val Phe Gln Gly Asn Gln Asp
        2275                2280                2285

Ser Phe Thr Pro Val Val Asn Ser Leu Asp Pro Pro Leu Leu Thr Arg
    2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
                2325                2330
```